US012594260B2

(12) United States Patent
Stoller

(10) Patent No.: US 12,594,260 B2
(45) Date of Patent: Apr. 7, 2026

(54) TOPICAL FORMULATIONS FOR INFECTIONS

(71) Applicant: Topical Rx, LLC, Tulsa, OK (US)

(72) Inventor: David A. Stoller, Tulsa, OK (US)

(73) Assignee: Topical Rx, LLC, Tulsa, OK (US)

( * ) Notice: Subject to any disclaimer, the term of this patent is extended or adjusted under 35 U.S.C. 154(b) by 0 days.

(21) Appl. No.: 18/759,222

(22) Filed: Jun. 28, 2024

(65) Prior Publication Data

US 2026/0000649 A1 Jan. 1, 2026

(51) Int. Cl.
| | |
|---|---|
| *A61K 31/4174* | (2006.01) |
| *A61K 31/137* | (2006.01) |
| *A61K 31/351* | (2006.01) |
| *A61K 31/573* | (2006.01) |
| *A61P 31/10* | (2006.01) |

(52) U.S. Cl.
CPC ........ *A61K 31/4174* (2013.01); *A61K 31/137* (2013.01); *A61K 31/351* (2013.01); *A61K 31/573* (2013.01); *A61P 31/10* (2018.01)

(58) Field of Classification Search
None
See application file for complete search history.

(56) References Cited

U.S. PATENT DOCUMENTS

| | | | | |
|---|---|---|---|---|
| 2002/0037884 A1* | 3/2002 | Singh | ................... | A61K 31/545 |
| | | | | 514/200 |
| 2009/0143479 A1* | 6/2009 | Bonny | ................. | A61K 9/0056 |
| | | | | 514/649 |
| 2017/0281677 A1 | 10/2017 | Spurgeon et al. | | |
| 2017/0333466 A1 | 11/2017 | Ray, II | | |
| 2018/0228760 A1* | 8/2018 | Dunman | ................ | A61K 47/10 |
| 2022/0265694 A1* | 8/2022 | Ray, II | ................. | A61K 31/573 |

FOREIGN PATENT DOCUMENTS

RU 2674765 C2 12/2018

OTHER PUBLICATIONS

Bubnis, Daniel. Home Remedies for Athlete's Foot. Retrieved from the internet on Aug. 18, 2024, https://www.healthline.com/health/home-remedies-for-athletes-foot. Published Feb. 1, 2023. (Year: 2023).*

Animax Ointment (Drug Information page, Manufactured by Fougera Pharmaceuticals, published Jan. 2023). (Year: 2023).*

Johnson MD, Perfect JR. Use of Antifungal Combination Therapy: Agents, Order, and Timing. Curr Fungal Infect Rep. May 1, 2010; 4(2):87-95. (Year: 2010).*

Elise Ekstrand, Daniela Esposito, Oskar Ragnarsson, Jörgen Isgaard, Gudmundur Johannsson, Metabolic Effects of Cortisone Acetate vs Hydrocortisone in Patients With Secondary Adrenal Insufficiency, Journal of the Endocrine Society, vol. 4, Issue 12, Dec. 2020, (Year: 2020).*

NIH National Cancer Institute. Acetic Acid. Retrieved from the Internet on Feb. 25, 2025, https://www.cancer.gov/publications/dictionaries/cancer-drug/def/acetic-acid. (Year: 2025).*

Chattem, Inc.; "CORTIZONE-10 Cooling Relief—Hydrocortisone Gel," Drug Label Information (Marketing Start Date: Oct. 1, 2008); [retrieved online Aug. 23, 2024] URL: https://dailymed.nlm.nih.gov/dailymed/fda/fdaDrugXsl.cfm?setid=bb3d1a3e-4c0c-4694-9c05-80152dd9bd1c&type=display; 22 pages.

E. Fougera & Co. a division of Fougera Pharmaceuticals Inc.; "CLOTRIMAZOLE Cream USP 1%," Drug Label Information (Marketing Start Date: Sep. 2, 2008); [retrieved online Aug. 23, 2024] URL: https://dailymed.nlm.nih.gov/dailymed/fda/fdaDrugXsl.cfm?setid=28fdc2c0-fd5f-4d98-a4e1-4702a430086a&type=display; 5 pages.

Glenmark Pharmaceuticals Inc., USA; "MUPIROCIN Cream," Drug Label Information (Marketing Start Date: Jan. 24, 2013); [retrieved online Aug. 23, 2024] URL: https://dailymed.nlm.nih.gov/dailymed/fda/fdaDrugXsl.cfm?setid=acd6e23e-d83f-4ed8-9c50-467ed422a8c4&type=display; 8 pages.

Stoller, D., Topical RX—178495—Receipt dated Feb. 9, 2024, for Purchase of Compounded Formulation Containing Mupirocin, Clotrimazole, Terbinafine, and Hydrocortisone from Economy Pharmacy Express, Prepared According to Specifications Provided by David Stoller, 1 page.

Stoller, D., Topical RX—Receipt for Sale of Composition Containing Mupirocin, Clotrimazole, Terbinafine, and Hydrocortisone dated Feb. 9, 2024, 1 page.

Taro Pharmaceuticals U.S.A., Inc .; "Terbinafine Hydrochloride Cream 1% Antifungal Cream," Drug Label Information (Marketing Start Date: Jul. 2, 2007); [retrieved online Aug. 23, 2024] URL: https://dailymed.nlm.nih.gov/dailymed/fda/fdaDrugXsl.cfm?setid=92b31fc4-0f02-4857-b11f-49b9f942ee84&type=display; 4 pages.

Gu, Y., et al.; "Arcanobacterium haemolyticum—Infection in an Immunocompetent Child," The Pediatric Infectious Disease Journal; 43(1):e28-e29 (Jan. 2024).

International Search Report and Written Opinion for International Application No. PCT/US2025/035529, mailed Sep. 9, 2025, 12 pages.

Archy Pharmaceuticals, Nigeria; Brand: Archy dermo-clear; "Multiaction Cream," Published Sep. 2017; Mintel, Mintel GNPD; 3 pages [Retrieved online Aug. 27, 2025] from URL: www.gnpd.com/sinatra/recordpage/5060833/.

Pemason, Nigeria; Brand: Pem-Bact; "3-in-1 Action Cream," Published Jan. 2018; Mintel, Mintel GNPD; 3 pages [Retrieved online Aug. 27, 2025] from URL: www.gnpd.com/sinatra/recordpage/5353291/.

(Continued)

*Primary Examiner* — James H Alstrum-Acevedo
*Assistant Examiner* — Lauren Wells
(74) *Attorney, Agent, or Firm* — Cooley LLP

(57) ABSTRACT

Described herein are topical compositions containing one or more of an antibacterial, an antifungal, and an anti-inflammatory, for use in supporting the health of a subject, including preventing or treating a fungal infection, a yeast infection, a bacterial infection, inflammation, or any combination thereof.

14 Claims, 3 Drawing Sheets

(56) References Cited

OTHER PUBLICATIONS

Sanofi-Aventis, Mexico; Brand: Astra-Zenica; "Xyloderm Cream," Published Jun. 2004; Mintel, Mintel GNPD; 2 pages [Retrieved online Aug. 27, 2025] from URL: www.gnpd.com/sinatra/recordpage/10172175/.

* cited by examiner

TOPICAL FORMULATIONS FOR INFECTIONS

BACKGROUND

There are a wide variety of skin and nail conditions, and many different active agents have been developed to treat them. However, skin and nail conditions are complex—with the potential occurrence of secondary infections in addition to the primary infection. Additionally, the presence of multiple infections may further create complications.

The standard treatments of skin and nail conditions have generally ignored this complexity and, instead, focus largely on the treatment of the primary infection. Standard treatments, which suggest the sparing use of antibacterial agents to limit the development of antibacterial resistance, often are especially inadequate for the treatment of secondary infections, which are generally bacterial in nature.

There, therefore, exists a need for compositions and methods that can effectively treat these complex combinations of infections.

SUMMARY

One aspect of the present disclosure relates to compositions formulated for topical use that comprise a first antibacterial, a first antifungal, and a first anti-inflammatory. In some embodiments, the first antibacterial is a topical antibacterial. In some embodiments, wherein the first antibacterial is mupirocin, neomycin, bacitracin, polymyxin B, sulfadiazine, clindamycin, gentamicin, erythromycin, or metronidazole, or a pharmaceutically acceptable salt thereof. In some embodiments, the first antibacterial is mupirocin or a pharmaceutically acceptable salt thereof. In some embodiments, the composition contains the first antibacterial in an amount of from about 0.05% v/v to about 2% v/v. In some embodiments, the composition contains the first antibacterial in an amount of about 0.5% v/v.

In some embodiments, the composition comprises a second antibacterial. In some embodiments, the composition contains the second antibacterial in an amount of from about 0.1% v/v to about 1% v/v. In some embodiments, the composition contains the second antibacterial in an amount of about 0.5% v/v. In some embodiments, the second antibacterial is mupirocin, bacitracin, polymyxin B, sulfadiazine, clindamycin, gentamicin, erythromycin, or metronidazole, or a pharmaceutically acceptable salt thereof.

In some embodiments, the first antifungal is a topical antifungal. In some embodiments, the first antifungal is butenafine, ciclopirox, clotrimazole, econazole, ketoconazole, miconazole, naftifine, nystatin, oxiconazole, sertaconazole, terbinafine, or tolnaftate, or a pharmaceutically acceptable salt thereof. In some embodiments, the first antifungal is terbinafine or clotrimazole, or a pharmaceutically acceptable salt thereof. In some embodiments, the composition contains the first antifungal in an amount of from about 0.05% v/v to about 1.0% v/v. In some embodiments, the composition contains the first antifungal in an amount of about 0.25% v/v.

In some embodiments, the composition comprises a second antifungal. In some embodiments, the second antifungal is butenafine, ciclopirox, clotrimazole, econazole, ketoconazole, miconazole, naftifine, nystatin, oxiconazole, sertaconazole, terbinafine, or tolnaftate, or a pharmaceutically acceptable salt thereof. In some embodiments, the first antifungal is terbinafine, or a pharmaceutically acceptable salt thereof, and the second antifungal is clotrimazole, or a pharmaceutically acceptable salt thereof. In some embodiments, the composition contains the second antifungal in an amount of from about 0.05% v/v to about 1.0% v/v. In some embodiments, the composition contains the second antifungal in an amount of about 0.25% v/v.

In some embodiments, the first anti-inflammatory is a topical anti-inflammatory. In some embodiments, the first anti-inflammatory is a corticosteroid. In some embodiments, the first anti-inflammatory is hydrocortisone, alclometasone, clocortolone, desonide, bethamethasone, fluocinolone, or triamcinolone, or a pharmaceutically acceptable salt thereof. In some embodiments, the first anti-inflammatory is hydrocortisone or a pharmaceutically acceptable salt thereof. In some embodiments, the first anti-inflammatory is hydrocortisone acetate. In some embodiments, the composition contains the first anti-inflammatory in an amount of from about 0.05% v/v to about 1.0% v/v. In some embodiments, the composition contains the first anti-inflammatory in an amount of about 0.25% v/v.

In some embodiments, comprising a second anti-inflammatory. In some embodiments, the composition contains the second anti-inflammatory in an amount of from about 0.05% v/v to about 1.0% v/v. In some embodiments, the composition contains the second anti-inflammatory in an amount of about 0.5% v/v. In some embodiments, the second anti-inflammatory is hydrocortisone, alclometasone, clocortolone, desonide, bethamethasone, fluocinolone, or triamcinolone, or a pharmaceutically acceptable salt thereof.

In some embodiments, the composition comprises mupirocin, terbinafine, clotrimazole, and hydrocortisone, or pharmaceutically acceptable salts thereof. In some embodiments, the composition consists essentially of mupirocin, terbinafine, clotrimazole, and hydrocortisone, or pharmaceutically acceptable salts thereof. In some embodiments, the composition contains the mupirocin in an amount of 0.5% v/v. In some embodiments, the composition contains the terbinafine in an amount of 0.25% v/v. In some embodiments, the composition contains the clotrimazole in an amount of 0.25% v/v. In some embodiments, the composition contains the hydrocortisone in an amount of 0.25% v/v.

Another aspect of the present disclosure relates to a composition formulated for topical use comprising mupirocin, or a pharmaceutically acceptable salt thereof, in an amount of between about 0.2 and about 0.75% v/v, terbinafine, or a pharmaceutically acceptable salt thereof, in an amount between about 0.1 and about 0.5% v/v, clotrimazole, or a pharmaceutically acceptable salt thereof, in an amount between about 0.1 and about 0.5% v/v, and hydrocortisone, or a pharmaceutically acceptable salt thereof, in an amount between about 0.1 and about 0.5% v/v. In some embodiments, the composition consists essentially of about 0.5% v/v of the mupirocin, or the pharmaceutically acceptable salt thereof, about 0.25% v/v of the terbinafine, or the pharmaceutically acceptable salt thereof, about 0.25% v/v of the clotrimazole, or the pharmaceutically acceptable salt thereof, and about 0.25% v/v of the hydrocortisone, or the pharmaceutically acceptable salt thereof.

Another aspect of the present disclosure relates to a composition formulated for topical use, comprising mupirocin calcium in an amount of 0.5% v/v, terbinafine hydrochloride in an amount of 0.25% v/v, clotrimazole in an amount of 0.25% v/v, and hydrocortisone acetate in an amount of 0.25% v/v. In some embodiments, the composition consists essentially of the mupirocin calcium, terbinafine hydrochloride, clotrimazole, and hydrocortisone acetate.

In some embodiments, the composition is in the form of a cream, an ointment, a lotion, or a gel. In some embodiments, the composition is in the form of a cream. In some embodiments, the composition is for use as a medicament. In some embodiments, the composition is for use in treating a fungal infection, a yeast infection, a bacterial infection, inflammation, or any combination thereof. In some embodiments, the composition is for use in treating athlete's foot, jock itch, or ringworm. In some embodiments, the composition is for use in treating athlete's foot.

Another aspect of the present disclosure relates to a method of preparing a composition, the method comprising combining the antibacterial, the antifungal, and the anti-inflammatory.

Another aspect of the present disclosure relates to a method of treating or preventing a fungal infection, a yeast infection, a bacterial infection, inflammation, or any combination thereof, the method comprising topically administering to a subject a composition. In some embodiments, the method treats or prevents athlete's foot, jock itch, or ringworm. In some embodiments, the method treats or prevents athlete's foot. In some embodiments, the method treats athlete's foot. In some embodiments, the method comprises administering the composition once daily, twice daily, or three times daily. In some embodiments, the administration is performed for a duration of from about 1 day to about 4 weeks. In some embodiments, the administration is performed for a duration of about 1 week, about 10 days, about 2 weeks, about 3 weeks, or about 4 weeks.

Another aspect of the present disclosure relates to a composition for the treatment of athlete's foot, jock itch, or ringworm. In some embodiments, the composition is used for the treatment of athlete's foot.

Another aspect of the present disclosure relates to use of a first antibacterial, a first antifungal, and a first anti-inflammatory for the manufacture of a medicament for the treatment or prevention of a fungal infection, a yeast infection, a bacterial infection, inflammation, or any combination thereof. In some embodiments, the medicament is for the treatment or prevention of athlete's foot, jock itch, or ringworm. In some embodiments, the medicament is for the treatment or prevention of athlete's foot. In some embodiments, the medicament is for the treatment of athlete's foot.

Other objects and advantages of the present disclosure will become apparent from the detailed description that follows.

DETAILED DESCRIPTION

Figure 1A:
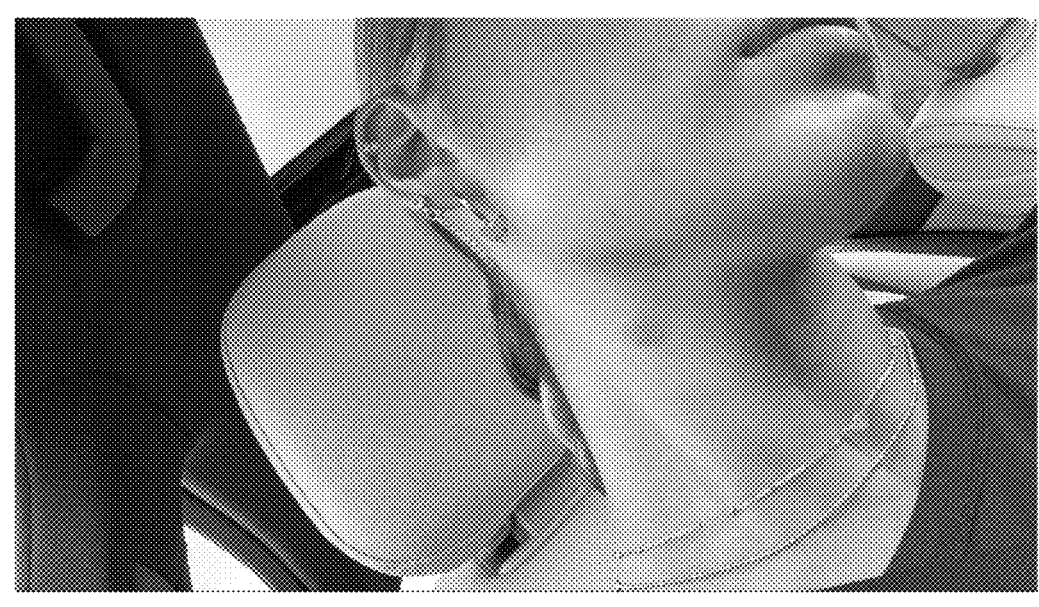
FIGS. 1A and 1B show the subject of Example 2's affected neck both before (FIG. 1A; photo dated May 1, 2024) and after (FIG. 1B; photo dated May 11, 2024) treatment with Exemplary Composition 1.

The following description sets forth numerous exemplary configurations, methods, parameters, and the like. It should be recognized, however, that such description is not intended as a limitation on the scope of the present disclosure but is instead provided as a description of exemplary embodiments.

The present disclosure generally provides compositions that contain multiple active agents for the treatment of complex skin and nail conditions, and related methods. In some embodiments, the compositions may contain antifungal, antibacterial, and anti-inflammatory agents in order to effectively treat complex combinations of infections. Without being bound by any theory or mechanism, the combination of antifungal, antibacterial, and anti-inflammatory agents included in the compositions herein may have unexpected synergistic effects that allow for effective treatment.

Definitions

As used herein, the indefinite articles "a" and "an" and the definite article "the" are intended to include both the singular and the plural, unless the context in which they are used clearly indicates otherwise. "At least one" and "one or more" are used interchangeably to mean that the article may include one or more than one of the listed elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents. Unless otherwise indicated, it is to be understood that all numbers expressing quantities, ratios, and numerical properties of ingredients, reaction conditions, and so forth, used in the specification and claims are contemplated to be able to be modified in all instances by the term "about."

"Physiologically acceptable," "pharmaceutically acceptable," or "pharmacologically acceptable" compounds and compositions may include materials which are not biologically, or otherwise, undesirable. For example, a pharmaceutically acceptable salt is a salt that may be administered to an individual without causing any substantially undesirable biological effects or interacting in a deleterious manner with any of the components of the composition in which it is contained.

As used herein, "preventing" a condition refers to reducing the probability that a subject develops or redevelops such condition, or that an existing condition spreads further.

As used herein, "treating" a condition refers to eliminating, reducing, or ameliorating one or more symptoms associated with a condition.

A "volume fraction" or "volume percent" refers to the ratio of the volume of a substance within a mixture to the total volume of the mixture. Volume fractions or volume percents may be represented, for example, by v/v, % v/v, or vol %.

A "weight fraction" or "weight percent" refers to the ratio of the weight of a substance within a mixture to the total mass of the mixture. Weight fractions or weight percents may be represented, for example, by w/w, % w/w, or wt %.

Compositions

Provided herein are topical compositions useful for the treatment or prevention of skin or nail conditions. Topical compositions are compositions that may be administered topically—that is, applied directly to the skin, nail, or mucous membrane of a subject. In some embodiments, topical compositions contain one or more components that can be effectively delivered to the subject via topical administration. In some embodiments, topical compositions are formulated for administration directly to the subject's skin, nails, or both skin and nails.

In some embodiments, the composition is a cream, an ointment, a lotion, a gel, a spray, or a powder. In some embodiments, the composition is a cream or a lotion. In certain embodiments, the composition is a cream.

In some embodiments, the composition comprises one or more active ingredients. As used herein, the terms "active ingredient" and "active agent" both refer to a component of a composition described herein intended to have a desired effect (e.g., providing a health benefit). The term encompasses any molecule, chemical, composition, drug, active ingredient, or biological agent for preventing or treating a condition in an individual. Further, the term encompasses small molecules (e.g., compounds having a molecular weight of less than about 1 kDa), peptides, proteins, inorganic compounds, alloys of inorganic compounds, carbohydrates, lipids, and combinations thereof. In some embodiments, the active ingredient is a naturally occurring substance or a derivative thereof. In some embodiments, the active ingredient is a synthetic (e.g., chemically synthesized) substance. In some embodiments, the active ingredient is recombinantly produced.

In some embodiments, the composition comprises one or more, two or more, three or more, four or more, five or more, six or more, seven or more, eight or more, nine or more, or ten or more active ingredients. In some embodiments, the composition comprises one, two, three, four, five, six, seven, eight, nine, ten, or more than ten active ingredients. In some embodiments, the composition comprises at least one, at least two, at least three, at least four, at least five, at least six, at least seven, at least eight, at least nine, or at least ten active ingredients.

The active ingredients of the compositions of the present disclosure may include, but are not limited to, antifungals, antibacterials, antivirals, anti-inflammatoireantihistamines, anesthetics, emollients, keratolytics, and rubefacients.

In some embodiments, the composition comprises one or more of an antifungal, an antibacterial, and an anti-inflammatory. In some embodiments, the composition comprises two or more of an antifungal, an antibacterial, and an anti-inflammatory. In some embodiments, the composition comprises each of an antifungal, an antibacterial, and an anti-inflammatory.

A. Antibacterials

As used herein, an antibacterial (also known as an antibiotic) is an active agent that kills or inhibits the growth of certain bacteria. An antibacterial that kills bacteria may also be known as a bactericide or a bacteriocide. An antibacterial that inhibits bacterial growth may also be known as a bacteriostatic. An antibacterial may treat or prevent a bacterial infection.

In some embodiments, the composition comprises one or more, two or more, three or more, or four or more antibacterials. In some embodiments, the composition comprises one, two, three, four, or more than four antibacterials.

In some embodiments, the antibacterial is a topical antibacterial—that is, an antibacterial that may be administered topically.

Antibacterials of the present disclosure include, but are not limited to, mupirocin, neomycin, bacitracin, polymyxin B, sulfadiazine, clindamycin, gentamicin, erythromycin, or metronidazole, or a pharmaceutically acceptable salt thereof. In exemplary embodiments, the antibacterial is mupirocin, bacitracin, or polymyxin B, or a pharmaceutically acceptable salt thereof.

In some embodiments, the antibacterial is mupirocin or a pharmaceutically acceptable salt thereof. In some embodiments, the mupirocin, or the pharmaceutically acceptable salt thereof, is in a crystalline form. In some embodiments, the antibacterial is mupirocin free acid. In some embodiments, the antibacterial is mupirocin calcium. In some embodiments, the mupirocin calcium is mupirocin calcium dihydrate.

In some embodiments, the antibacterial is bacitracin or a pharmaceutically acceptable salt thereof. In some embodiments, the bacitracin, or the pharmaceutically acceptable salt thereof, is in a crystalline form. In some embodiments, the antibacterial is bacitracin free acid. In some embodiments, the antibacterial is bacitracin zinc.

In some embodiments, the antibacterial is polymyxin B or a pharmaceutically acceptable salt thereof. In some embodiments, the polymyxin B, or the pharmaceutically acceptable salt thereof, is in a crystalline form. In some embodiments, the antibacterial is polymyxin B free base. In some embodiments, the antibacterial is polymyxin B sulfate.

In some embodiments, the composition comprises a first antibacterial. In some embodiments, the first antibacterial is mupirocin, neomycin, bacitracin, polymyxin B, sulfadiazine, clindamycin, gentamicin, erythromycin, or metronidazole, or a pharmaceutically acceptable salt thereof. In some embodiments, the first antibacterial is mupirocin, bacitracin, or polymyxin B, or a pharmaceutically acceptable salt thereof.

In some embodiments, the first antibacterial is mupirocin or a pharmaceutically acceptable salt thereof. In some embodiments, the mupirocin, or the pharmaceutically acceptable salt thereof, is in a crystalline form. In some embodiments, the first antibacterial is mupirocin free acid. In some embodiments, the first antibacterial is mupirocin calcium. In some embodiments, the mupirocin calcium is mupirocin calcium dihydrate.

In some embodiments, the first antibacterial is bacitracin or a pharmaceutically acceptable salt thereof. In some embodiments, the bacitracin, or the pharmaceutically acceptable salt thereof, is in a crystalline form. In some embodiments, the first antibacterial is bacitracin free acid. In some embodiments, the first antibacterial is bacitracin zinc.

In some embodiments, the first antibacterial is polymyxin B or a pharmaceutically acceptable salt thereof. In some embodiments, the polymyxin B, or the pharmaceutically acceptable salt thereof, is in a crystalline form. In some embodiments, the first antibacterial is polymyxin B free base. In some embodiments, the first antibacterial is polymyxin B sulfate.

In some embodiments, the composition contains the first antibacterial in an amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the first antibacterial in an amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first antibacterial in an amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the first antibacterial in an amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the composition comprises the first antibacterial and a second antibacterial. In some embodiments, the first antibacterial is different from the second antibacterial. The second antibacterial may be, but is not limited to, one of the antibacterial agents previously described herein. The composition may contain the second antibacterial in an amount previously described herein.

In some embodiments, the second antibacterial is mupirocin, neomycin, bacitracin, polymyxin B, sulfadiazine, clindamycin, gentamicin, erythromycin, or metronidazole, or a pharmaceutically acceptable salt thereof. In some embodiments, the second antibacterial is mupirocin, bacitracin, or polymyxin B, or a pharmaceutically acceptable salt thereof.

In some embodiments, the second antibacterial is mupirocin or a pharmaceutically acceptable salt thereof. In some embodiments, the mupirocin, or the pharmaceutically acceptable salt thereof, is in a crystalline form. In some embodiments, the second antibacterial is mupirocin free acid. In some embodiments, the second antibacterial is mupirocin calcium. In some embodiments, the mupirocin calcium is mupirocin calcium dihydrate.

In some embodiments, the second antibacterial is bacitracin or a pharmaceutically acceptable salt thereof. In some embodiments, the bacitracin, or the pharmaceutically acceptable salt thereof, is in a crystalline form. In some embodiments, the second antibacterial is bacitracin free acid. In some embodiments, the second antibacterial is bacitracin zinc.

In some embodiments, the second antibacterial is polymyxin B or a pharmaceutically acceptable salt thereof. In some embodiments, the polymyxin B, or the pharmaceutically acceptable salt thereof, is in a crystalline form. In some embodiments, the second antibacterial is polymyxin B free base. In some embodiments, the second antibacterial is polymyxin B sulfate.

In some embodiments, the composition contains the second antibacterial in an amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the second antibacterial in an amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the second antibacterial in an amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the second antibacterial in an amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the first antibacterial is mupirocin, or a pharmaceutically acceptable salt thereof, and the second antibacterial is neomycin, bacitracin, polymyxin B, sulfadiazine, clindamycin, gentamicin, erythromycin, or metronidazole, or a pharmaceutically acceptable salt thereof. In some embodiments, the mupirocin, or the pharmaceutically acceptable salt thereof, is in a crystalline form. In some embodiments, the first antibacterial is mupirocin free acid and the second antibacterial is neomycin, bacitracin, polymyxin B, sulfadiazine, clindamycin, gentamicin, erythromycin, or metronidazole, or a pharmaceutically acceptable salt thereof. In some embodiments, the first antibacterial is mupirocin calcium and the second antibacterial is neomycin, bacitracin, polymyxin B, sulfadiazine, clindamycin, gentamicin, erythromycin, or metronidazole, or a pharmaceutically acceptable salt thereof. In some embodiments, the first antibacterial is mupirocin calcium dihydrate and the second antibacterial is neomycin, bacitracin, polymyxin B, sulfadiazine, clindamycin, gentamicin, erythromycin, and metronidazole, or a pharmaceutically acceptable salt thereof.

In some embodiments, the first antibacterial is bacitracin, or a pharmaceutically acceptable salt thereof, and the second antibacterial is mupirocin, neomycin, polymyxin B, sulfadiazine, clindamycin, gentamicin, erythromycin, or metronidazole, or a pharmaceutically acceptable salt thereof. In some embodiments, the bacitracin, or the pharmaceutically acceptable salt thereof, is in a crystalline form. In some embodiments, the first antibacterial is bacitracin free acid and the second antibacterial is mupirocin, neomycin, poly-myxin B, sulfadiazine, clindamycin, gentamicin, erythromycin, or metronidazole, or a pharmaceutically acceptable salt thereof. In some embodiments, the first antibacterial is bacitracin zinc and the second antibacterial is mupirocin, neomycin, polymyxin B, sulfadiazine, clindamycin, gentamicin, erythromycin, or metronidazole, or a pharmaceutically acceptable salt thereof.

In some embodiments, the erythromycin, or the pharmaceutically acceptable salt thereof, is erythromycin base.

In some embodiments, the composition contains the first antibacterial and the second antibacterial in a combined amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the first antibacterial and the second antibacterial in a combined amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first antibacterial and the second antibacterial in a combined amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the first antibacterial and the second antibacterial in a combined amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the composition comprises a first antibacterial, a second antibacterial, and a third antibacterial. In some embodiments, the first antibacterial, the second antibacterial, and the third antibacterial are each different from each other. The third antibacterial may be, but is not limited to, one of the antibacterial agents previously described herein. The composition may contain the third antibacterial in an amount previously described herein.

In some embodiments, the first antibacterial is bacitracin, or a pharmaceutically acceptable salt thereof, the second antibacterial is polymyxin B, or a pharmaceutically acceptable salt thereof, and the third antibacterial is mupirocin, neomycin, sulfadiazine, clindamycin, gentamicin, erythromycin, or metronidazole, or a pharmaceutically acceptable salt thereof. the first antibacterial is bacitracin free acid, the second antibacterial is polymyxin B, or a pharmaceutically acceptable salt thereof, and the third antibacterial is mupirocin, neomycin, sulfadiazine, clindamycin, gentamicin, erythromycin, or metronidazole, or a pharmaceutically acceptable salt thereof, the first antibacterial is bacitracin zinc, the second antibacterial is polymyxin B, or a pharmaceutically acceptable salt thereof, and the third antibacterial is mupirocin, neomycin, sulfadiazine, clindamycin, gentamicin, erythromycin, or metronidazole, or a pharmaceutically acceptable salt thereof. In some embodiments, the first antibacterial is bacitracin, or a pharmaceutically acceptable salt thereof, the second antibacterial is polymyxin B free base, and the third antibacterial is mupirocin, neomycin, sulfadiazine, clindamycin, gentamicin, erythromycin, or metronidazole, or a pharmaceutically acceptable salt thereof. In some embodiments, the first antibacterial is bacitracin, or a pharmaceutically acceptable salt thereof, the second antibacterial is polymyxin B sulfate, and the third antibacterial is mupirocin, neomycin, sulfadiazine, clindamycin, gentamicin, erythromycin, and metronidazole, or a pharmaceutically acceptable salt thereof. In some embodiments, the first antibacterial is bacitracin free acid, the second antibacterial is polymyxin B free base, and the third antibacterial is mupirocin, neomycin, sulfadiazine, clindamycin, gentamicin, erythromycin, or metronidazole, or a pharmaceutically acceptable salt thereof. In some embodiments, the first antibacterial is bacitracin free acid, the second antibacterial is polymyxin B sulfate, and the third antibacterial is mupirocin, neomycin, sulfadiazine, clindamycin, gentamicin, erythromycin, or metronidazole, or a pharmaceutically acceptable salt thereof. In some embodiments, the first antibacterial is bacitracin zinc, the second antibacterial is polymyxin B free base, and the third antibacterial is mupirocin, neomycin, sulfadiazine, clindamycin, gentamicin, erythromycin, and metronidazole, or pharmaceutically acceptable salts thereof. In some embodiments, the first antibacterial is bacitracin zinc, the second antibacterial is polymyxin B sulfate, and the third antibacterial is mupirocin, neomycin, sulfadiazine, clindamycin, gentamicin, erythromycin, or metronidazole, or a pharmaceutically acceptable salt thereof.

In some embodiments, the composition comprises a first antibacterial, a second antibacterial, a third antibacterial, and a fourth antibacterial. In some embodiments, the first antibacterial, the second antibacterial, the third antibacterial, and the fourth antibacterial are each different from each other. The fourth antibacterial may be, but is not limited to, one of the antibacterial agents previously described herein. The composition may contain the fourth antibacterial in an amount previously described herein.

In some embodiments, the composition contains the first antibacterial, the second antibacterial, and the third antibacterial, or the first antibacterial, the second antibacterial, the third antibacterial, and the fourth antibacterial, in a combined amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the first antibacterial, the second antibacterial, and the third antibacterial, or the first antibacterial, the second antibacterial, the third antibacterial, and the fourth antibacterial, in a combined amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first antibacterial, the second antibacterial, and the third antibacterial, or the first antibacterial, the second antibacterial, the third antibacterial, and the fourth antibacterial, in a combined amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the first antibacterial, the second antibacterial, and the third antibacterial, or the first antibacterial, the second antibacterial, the third antibacterial, and the fourth antibacterial, in a combined amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

B. Antifungals

As used herein, an antifungal is an active agent that kills or inhibits the growth of certain fungi. An antifungal that kills fungi may also be known as fungicide. An antifungal that inhibits fungal growth may also be known as a fungistatic. An antifungal may treat or prevent a fungal infection.

In some embodiments, the composition comprises one or more, two or more, three or more, or four or more antifungals. In some embodiments, the composition comprises one, two, three, four, or more than four antifungals.

In some embodiments, the antifungal is a topical antifungal—that is, an antifungal that may be administered topically.

Antifungals of the present disclosure may be, but are not limited to, butenafine, ciclopirox, clotrimazole, econazole, ketoconazole, miconazole, naftifine, nystatin, oxiconazole, sertaconazole, terbinafine, or tolnaftate, or a pharmaceutically acceptable salt thereof. In some embodiments, the antifungal is clotrimazole, miconazole, nystatin, oxiconazole, or terbinafine, or a pharmaceutically acceptable salt thereof. In exemplary embodiments, the antifungal is clotrimazole or terbinafine, or a pharmaceutically acceptable salt thereof.

In some embodiments, the antifungal is clotrimazole or a pharmaceutically acceptable salt thereof. In some embodiments, the clotrimazole, or the pharmaceutically acceptable salt thereof, is in a crystalline form. In some embodiments, the antifungal is clotrimazole free base.

In some embodiments, the antifungal is terbinafine or a pharmaceutically acceptable salt thereof. In some embodiments, the terbinafine, or the pharmaceutically acceptable salt thereof, is in a crystalline form. In some embodiments, the antifungal is terbinafine free base. In some embodiments, the antifungal is terbinafine hydrochloride.

In some embodiments, the antifungal is miconazole or a pharmaceutically acceptable salt thereof. In some embodiments, the miconazole, or the pharmaceutically acceptable salt thereof, is in a crystalline form. In some embodiments, the antifungal is miconazole free base. In some embodiments, the antifungal is miconazole nitrate.

In some embodiments, the antifungal is nystatin or a pharmaceutically acceptable salt thereof. In some embodiments, the nystatin, or the pharmaceutically acceptable salt thereof, is in a crystalline form. In some embodiments, the antifungal is nystatin free acid.

In some embodiments, the antifungal is oxiconazole or a pharmaceutically acceptable salt thereof. In some embodiments, the oxiconazole, or the pharmaceutically acceptable salt thereof, is in a crystalline form. In some embodiments, the antifungal is oxiconazole free base. In some embodiments, the antifungal is oxiconazole nitrate.

In some embodiments, the composition comprises a first antifungal. In some embodiments, the first antifungal is butenafine, ciclopirox, clotrimazole, econazole, ketoconazole, miconazole, naftifine, nystatin, oxiconazole, sertaconazole, terbinafine, or tolnaftate, or a pharmaceutically acceptable salt thereof. In some embodiments, the antifungal is clotrimazole, miconazole, nystatin, oxiconazole, or terbinafine, or a pharmaceutically acceptable salt thereof. In exemplary embodiments, the antifungal is clotrimazole or terbinafine, or a pharmaceutically acceptable salt thereof.

In some embodiments, the first antifungal is clotrimazole or a pharmaceutically acceptable salt thereof. In some embodiments, the clotrimazole, or the pharmaceutically acceptable salt thereof, is in a crystalline form. In some embodiments, the first antifungal is clotrimazole free base.

In some embodiments, the first antifungal is terbinafine or a pharmaceutically acceptable salt thereof. In some embodiments, the terbinafine, or the pharmaceutically acceptable salt thereof, is in a crystalline form. In some embodiments, the first antifungal is terbinafine free base. In some embodiments, the first antifungal is terbinafine hydrochloride.

In some embodiments, the first antifungal is miconazole or a pharmaceutically acceptable salt thereof. In some embodiments, the miconazole, or the pharmaceutically acceptable salt thereof, is in a crystalline form. In some embodiments, the first antifungal is miconazole free base. In some embodiments, the first antifungal is miconazole nitrate.

In some embodiments, the first antifungal is nystatin or a pharmaceutically acceptable salt thereof. In some embodiments, the nystatin, or the pharmaceutically acceptable salt thereof, is in a crystalline form. In some embodiments, the first antifungal is nystatin free acid.

In some embodiments, the first antifungal is oxiconazole or a pharmaceutically acceptable salt thereof. In some embodiments, the oxiconazole, or the pharmaceutically acceptable salt thereof, is in a crystalline form. In some embodiments, the first antifungal is oxiconazole free base. In some embodiments, the first antifungal is oxiconazole nitrate.

In some embodiments, the composition contains the first antifungal in an amount between about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.35% v/v, about 0.01 and about 0.3% v/v, about 0.01 and about 0.25% v/v, about 0.01 and about 0.2% v/v, about 0.01 and about 0.15% v/v, about 0.01 and about 0.1% v/v, about 0.01 and about 0.05% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.35% v/v, about 0.05 and about 0.3% v/v, about 0.05 and about 0.25% v/v, about 0.05 and about 0.2% v/v, about 0.05 and about 0.15% v/v, about 0.05 and about 0.1% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.35% v/v, about 0.1 and about 0.3% v/v, about 0.1 and about 0.25% v/v, about 0.1 and about 0.2% v/v, about 0.1 and about 0.15% v/v, about 0.15 and about 2% v/v, about 0.15 and about 1% v/v, about 0.15 and about 0.75% v/v, about 0.15 and about 0.6% v/v, about 0.15 and about 0.5% v/v, about 0.15 and about 0.4% v/v, about 0.15 and about 0.35% v/v, about 0.15 and about 0.3% v/v, about 0.15 and about 0.25% v/v, about 0.15 and about 0.2% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.35% v/v, about 0.2 and about 0.3% v/v, about 0.2 and about 0.25% v/v, about 0.25 and about 2% v/v, about 0.25 and about 1% v/v, about 0.25 and about 0.75% v/v, about 0.25 and about 0.6% v/v, about 0.25 and about 0.5% v/v, about 0.25 and about 0.4% v/v, about 0.25 and about 0.35% v/v, about 0.25 and about 0.3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.3 and about 0.35% v/v, about 0.35 and about 2% v/v, about 0.35 and about 1% v/v, about 0.35 and about 0.75% v/v, about 0.35 and about 0.6% v/v, about 0.35 and about 0.5% v/v, about 0.35 and about 0.4% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 2% v/v, about 0.5 and about 1% v/v, about 0.5 and about 0.75% v/v, about 0.5 and about 0.6% v/v, about 0.6 and about 2% v/v, about 0.6 and about 1% v/v, about 0.6 and about 0.75% v/v, about 0.75 and about 2% v/v, about 0.75 and about 1% v/v, or about 1 and about 2% v/v.

In exemplary embodiments, the composition contains the first antifungal in an amount of about 0.01% v/v, about 0.05% v/v, about 0.1% v/v, about 0.15% v/v, about 0.2% v/v, about 0.25% v/v, about 0.3% v/v, about 0.35% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first antifungal in an amount between about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.35% w/w, about 0.01 and about 0.3% w/w, about 0.01 and about 0.25% w/w, about 0.01 and about 0.2% w/w, about 0.01 and about 0.15% w/w, about 0.01 and about 0.1% w/w, about 0.01 and about 0.05% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.35% w/w, about 0.05 and about 0.3% w/w, about 0.05 and about 0.25% w/w, about 0.05 and about 0.2% w/w, about 0.05 and about 0.15% w/w, about 0.05 and about 0.1% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.35% w/w, about 0.1 and about 0.3% w/w, about 0.1 and about 0.25% w/w, about 0.1 and about 0.2% w/w, about 0.1 and about 0.15% w/w, about 0.15 and about 2% w/w, about 0.15 and about 1% w/w, about 0.15 and about 0.75% w/w, about 0.15 and about 0.6% w/w, about 0.15 and about 0.5% w/w, about 0.15 and about 0.4% w/w, about 0.15 and about 0.35% w/w, about 0.15 and about 0.3% w/w, about 0.15 and about 0.25% w/w, about 0.15 and about 0.2% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.35% w/w, about 0.2 and about 0.3% w/w, about 0.2 and about 0.25% w/w, about 0.25 and about 2% w/w, about 0.25 and about 1% w/w, about 0.25 and about 0.75% w/w, about 0.25 and about 0.6% w/w, about 0.25 and about 0.5% w/w, about 0.25 and about 0.4% w/w, about 0.25 and about 0.35% w/w, about 0.25 and about 0.3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.3 and about 0.35% w/w, about 0.35 and about 2% w/w, about 0.35 and about 1% w/w, about 0.35 and about 0.75% w/w, about 0.35 and about 0.6% w/w, about 0.35 and about 0.5% w/w, about 0.35 and about 0.4% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 2% w/w, about 0.5 and about 1% w/w, about 0.5 and about 0.75% w/w, about 0.5 and about 0.6% w/w, about 0.6 and about 2% w/w, about 0.6 and about 1% w/w, about 0.6 and about 0.75% w/w, about 0.75 and about 2% w/w, about 0.75 and about 1% w/w, or about 1 and about 2% w/w.

In exemplary embodiments, the composition contains the first antifungal in an amount of about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the composition comprises the first antifungal and a second antifungal. In some embodiments, the first antifungal is different from the second antifungal. The second antifungal may be, but is not limited to, one of the antifungal agents previously described herein. The composition may contain the second antifungal in an amount previously described herein.

In some embodiments, the second antifungal is butenafine, ciclopirox, clotrimazole, econazole, ketoconazole, miconazole, naftifine, nystatin, oxiconazole, sertaconazole, terbinafine, or tolnaftate, or a pharmaceutically acceptable salt thereof. In some embodiments, the second antifungal is clotrimazole, miconazole, nystatin, oxiconazole, or terbinafine, or a pharmaceutically acceptable salt thereof. In some embodiments, the second antifungal is clotrimazole or terbinafine, or a pharmaceutically acceptable salt thereof.

In some embodiments, the second antifungal is clotrimazole or a pharmaceutically acceptable salt thereof. In some embodiments, the clotrimazole, or the pharmaceutically acceptable salt thereof, is in a crystalline form. In some embodiments, the second antifungal is clotrimazole free base.

In some embodiments, the second antifungal is terbinafine or a pharmaceutically acceptable salt thereof. In some embodiments, the terbinafine, or the pharmaceutically acceptable salt thereof, is in a crystalline form. In some embodiments, the second antifungal is terbinafine free base. In some embodiments, the second antifungal is terbinafine hydrochloride.

In some embodiments, the second antifungal is miconazole or a pharmaceutically acceptable salt thereof. In some embodiments, the miconazole, or the pharmaceutically acceptable salt thereof, is in a crystalline form. In some embodiments, the second antifungal is miconazole free base. In some embodiments, the second antifungal is miconazole nitrate.

In some embodiments, the second antifungal is nystatin or a pharmaceutically acceptable salt thereof. In some embodiments, the nystatin, or the pharmaceutically acceptable salt thereof, is in a crystalline form. In some embodiments, the second antifungal is nystatin free acid.

In some embodiments, the second antifungal is oxiconazole or a pharmaceutically acceptable salt thereof. In some embodiments, the oxiconazole, or the pharmaceutically acceptable salt thereof, is in a crystalline form. In some embodiments, the second antifungal is oxiconazole free base. In some embodiments, the second antifungal is oxiconazole nitrate.

In some embodiments, the composition contains the second antifungal in an amount between about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.35% v/v, about 0.01 and about 0.3% v/v, about 0.01 and about 0.25% v/v, about 0.01 and about 0.2% v/v, about 0.01 and about 0.15% v/v, about 0.01 and about 0.1% v/v, about 0.01 and about 0.05% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.35% v/v, about 0.05 and about 0.3% v/v, about 0.05 and about 0.25% v/v, about 0.05 and about 0.2% v/v, about 0.05 and about 0.15% v/v, about 0.05 and about 0.1% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.35% v/v, about 0.1 and about 0.3% v/v, about 0.1 and about 0.25% v/v, about 0.1 and about 0.2% v/v, about 0.1 and about 0.15% v/v, about 0.15 and about 2% v/v, about 0.15 and about 1% v/v, about 0.15 and about 0.75% v/v, about 0.15 and about 0.6% v/v, about 0.15 and about 0.5% v/v, about 0.15 and about 0.4% v/v, about 0.15 and about 0.35% v/v, about 0.15 and about 0.3% v/v, about 0.15 and about 0.25% v/v, about 0.15 and about 0.2% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.35% v/v, about 0.2 and about 0.3% v/v, about 0.2 and about 0.25% v/v, about 0.25 and about 2% v/v, about 0.25 and about 1% v/v, about 0.25 and about 0.75% v/v, about 0.25 and about 0.6% v/v, about 0.25 and about 0.5% v/v, about 0.25 and about 0.4% v/v, about 0.25 and about 0.35% v/v, about 0.25 and about 0.3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.3 and about 0.35% v/v, about 0.35 and about 2% v/v, about 0.35 and about 1% v/v, about 0.35 and about 0.75% v/v, about 0.35 and about 0.6% v/v, about 0.35 and about 0.5% v/v, about 0.35 and about 0.4% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 2% v/v, about 0.5 and about 1% v/v, about 0.5 and about 0.75% v/v, about 0.5 and about 0.6% v/v, about 0.6 and about 2% v/v, about 0.6 and about 1% v/v, about 0.6 and about 0.75% v/v, about 0.75 and about 2% v/v, about 0.75 and about 1% v/v, or about 1 and about 2% v/v.

In exemplary embodiments, the composition contains the second antifungal in an amount of about 0.01% v/v, about 0.05% v/v, about 0.1% v/v, about 0.15% v/v, about 0.2% v/v, about 0.25% v/v, about 0.3% v/v, about 0.35% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the second antifungal in an amount between about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.35% w/w, about 0.01 and about 0.3% w/w, about 0.01 and about 0.25% w/w, about 0.01 and about 0.2% w/w, about 0.01 and about 0.15% w/w, about 0.01 and about 0.1% w/w, about 0.01 and about 0.05% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.35% w/w, about 0.05 and about 0.3% w/w, about 0.05 and about 0.25% w/w, about 0.05 and about 0.2% w/w, about 0.05 and about 0.15% w/w, about 0.05 and about 0.1% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.35% w/w, about 0.1 and about 0.3% w/w, about 0.1 and about 0.25% w/w, about 0.1 and about 0.2% w/w, about 0.1 and about 0.15% w/w, about 0.15 and about 2% w/w, about 0.15 and about 1% w/w, about 0.15 and about 0.75% w/w, about 0.15 and about 0.6% w/w, about 0.15 and about 0.5% w/w, about 0.15 and about 0.4% w/w, about 0.15 and about 0.35% w/w, about 0.15 and about 0.3% w/w, about 0.15 and about 0.25% w/w, about 0.15 and about 0.2% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.35% w/w, about 0.2 and about 0.3% w/w, about 0.2 and about 0.25% w/w, about 0.25 and about 2% w/w, about 0.25 and about 1% w/w, about 0.25 and about 0.75% w/w, about 0.25 and about 0.6% w/w, about 0.25 and about 0.5% w/w, about 0.25 and about 0.4% w/w, about 0.25 and about 0.35% w/w, about 0.25 and about 0.3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.3 and about 0.35% w/w, about 0.35 and about 2% w/w, about 0.35 and about 1% w/w, about 0.35 and about 0.75% w/w, about 0.35 and about 0.6% w/w, about 0.35 and about 0.5% w/w, about 0.35 and about 0.4% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 2% w/w, about 0.5 and about 1% w/w, about 0.5 and about 0.75% w/w, about 0.5 and about 0.6% w/w, about 0.6 and about 2% w/w, about 0.6 and about 1% w/w, about 0.6 and about 0.75% w/w, about 0.75 and about 2% w/w, about 0.75 and about 1% w/w, or about 1 and about 2% w/w.

In exemplary embodiments, the composition contains the second antifungal in an amount of about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the first antifungal is clotrimazole, or a pharmaceutically acceptable salt thereof, and the second antifungal is butenafine, ciclopirox, econazole, ketoconazole, miconazole, naftifine, nystatin, oxiconazole, sertaconazole, terbinafine, or tolnaftate or a pharmaceutically acceptable salt thereof. In some embodiments, the clotrimazole, or the pharmaceutically acceptable salt thereof, is in a crystalline form. In some embodiments, the first antifungal is clotrimazole free base and the second antifungal is butenafine, ciclopirox, econazole, ketoconazole, miconazole, naftifine, nystatin, oxiconazole, sertaconazole, terbinafine, or tolnaftate, or a pharmaceutically acceptable salt thereof.

In some embodiments, the first antifungal is terbinafine, or a pharmaceutically acceptable salt thereof, and the second antifungal is butenafine, ciclopirox, clotrimazole, econazole, ketoconazole, miconazole, naftifine, nystatin, oxiconazole, sertaconazole, or tolnaftate, or a pharmaceutically acceptable salt thereof. In some embodiments, the terbinafine, or the pharmaceutically acceptable salt thereof, is in a crystalline form. In some embodiments, the first antifungal is terbinafine free base and the second antifungal is butenafine, ciclopirox, clotrimazole, econazole, ketoconazole, miconazole, naftifine, nystatin, oxiconazole, sertaconazole, or tolnaftate, or a pharmaceutically acceptable salt thereof. In some embodiments, the first antifungal is terbinafine hydrochloride and the second antifungal is butenafine, ciclopirox, clotrimazole, econazole, ketoconazole, miconazole, naftifine, nystatin, oxiconazole, sertaconazole, or tolnaftate, or a pharmaceutically acceptable salt thereof In some embodiments, the first antifungal is clotrimazole, or a pharmaceutically acceptable salt thereof, and the second antifungal is terbinafine, or a pharmaceutically acceptable salt thereof. In some embodiments, one or both of the clotrimazole and the terbinafine are in a crystalline form. In some embodiments, the first antifungal is clotrimazole, or a pharmaceutically acceptable salt thereof, and the second antifungal is terbinafine free base. In some embodiments, the first antifungal is clotrimazole, or a pharmaceutically acceptable salt thereof, and the second antifungal is terbinafine hydrochloride. In some embodiments, the first antifungal is clotrimazole free base and the second antifungal is terbinafine, or a pharmaceutically acceptable salt thereof. In some embodiments, the first antifungal is clotrimazole free base and the second antifungal is terbinafine free base. In some embodiments, the first antifungal is clotrimazole free base and the second antifungal is terbinafine hydrochloride.

In some embodiments, the composition contains the first antifungal and the second antifungal in a combined amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the first antifungal and the second antifungal in a combined amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first antifungal and the second antifungal in a combined amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the first antifungal and the second antifungal in a combined amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the composition comprises a first antifungal, a second antifungal, and a third antifungal. In some embodiments, the first antifungal, the second antifungal, and the third antifungal are each different from each other. The third antifungal may be, but is not limited to, one of the antifungal agents previously described herein. The composition may contain the third anti-fungal in an amount previously described herein.

In some embodiments, the composition comprises a first antifungal, a second antifungal, a third antifungal, and a fourth antifungal. In some embodiments, the antifungal, the second antifungal, the third antifungal, and the fourth antifungal are each different from each other. The fourth antifungal may be, but is not limited to, one of the antifungal agents previously described herein. The composition may contain the fourth anti-fungal in an amount previously described herein.

In some embodiments, the composition contains the first antifungal, the second antifungal, and the third antifungal, or the first antifungal, the second antifungal, the third antifungal, and the fourth antifungal, in a combined amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the first antifungal, the second antifungal, and the third antifungal, or the first antifungal, the second antifungal, the third antifungal, and the fourth antifungal, in a combined amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first antifungal, the second antifungal, and the third antifungal, or the first antifungal, the second antifungal, the third antifungal, and the fourth antifungal, in a combined amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the first antifungal, the second antifungal, and the third antifungal, or the first antifungal, the second antifungal, the third antifungal, and the fourth antifungal, in a combined amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

C. Anti-Inflammatories

As used herein, an anti-inflammatory is an active agent that reduces inflammation or swelling. In some embodiments, an anti-inflammatory may, by reducing inflammation, reduce the amount of pain experienced by a subject. An anti-inflammatory may treat an inflammatory condition in a subject.

In some embodiments, the composition comprises one or more, two or more, three or more, or four or more anti-inflammatories. In some embodiments, the composition comprises one, two, three, four, or more than four anti-inflammatories.

In some embodiments, the anti-inflammatory is a topical anti-inflammatory—that is, an anti-inflammatory that may be administered topically.

In some embodiments, the anti-inflammatory is a corticosteroid. In some embodiments, the anti-inflammatory is a low potency corticosteroid (e.g., hydrocortisone, alclometasone, clocortolone, desonide, and the like). In some embodiments, the anti-inflammatory is a medium potency corticosteroid (e.g., bethamethasone, flucinolone, triamcinolone, and the like). Anti-inflammatories of the present disclosure include, but are not limited to, hydrocortisone, alclometasone, clocortolone, desonide, bethamethasone, fluocinolone, or triamcinolone, or a pharmaceutically acceptable salt thereof. In exemplary embodiments, the anti-inflammatory is hydrocortisone, fluocinolone, or triamcinolone, or a pharmaceutically acceptable salt thereof. In some embodiments, the anti-inflammatory is low potency hydrocortisone or a pharmaceutically acceptable salt thereof.

In some embodiments, the anti-inflammatory is hydrocortisone or a pharmaceutically acceptable salt thereof. In some embodiments, the hydrocortisone, or the pharmaceutically acceptable salt thereof, is in a crystalline form. In some embodiments, the anti-inflammatory is hydrocortisone free alcohol. In some embodiments, the anti-inflammatory is hydrocortisone acetate. In some embodiments, the anti-inflammatory is hydrocortisone valerate. In some embodiments, the anti-inflammatory is hydrocortisone sodium succinate. In some embodiments, the anti-inflammatory is hydrocortisone butyrate.

In some embodiments, the anti-inflammatory is fluocinolone or a pharmaceutically acceptable salt thereof. In some embodiments, the fluocinolone, or the pharmaceutically acceptable salt thereof, is in a crystalline form. In some embodiments, the anti-inflammatory is fluocinolone free alcohol. In some embodiments, the anti-inflammatory is fluocinolone acetonide.

In some embodiments, the anti-inflammatory is triamcinolone or a pharmaceutically acceptable salt thereof. In some embodiments, the triamcinolone, or the pharmaceutically acceptable salt thereof, is in a crystalline form. In some embodiments, the anti-inflammatory is triamcinolone free alcohol. In some embodiments, the anti-inflammatory is triamcinolone acetonide. In some embodiments, the anti-inflammatory is triamcinolone diacetate.

In some embodiments, the anti-inflammatory is alclometasone or a pharmaceutically acceptable salt thereof. In some embodiments, the alclometasone, or the pharmaceutically acceptable salt thereof, is in a crystalline form. In some embodiments, the anti-inflammatory is alclometasone free alcohol. In some embodiments, the anti-inflammatory is alclometasone dipropionate.

In some embodiments, the anti-inflammatory is clocortolone or a pharmaceutically acceptable salt thereof. In some embodiments, the clocortolone, or the pharmaceutically acceptable salt thereof, is in a crystalline form. In some embodiments, the anti-inflammatory is clocortolone free alcohol. In some embodiments, the anti-inflammatory is clocortolone pivalate.

In some embodiments, the anti-inflammatory is bethamethasone or a pharmaceutically acceptable salt thereof. In some embodiments, the bethamethasone, or the pharmaceutically acceptable salt thereof, is in a crystalline form. In some embodiments, the anti-inflammatory is bethamethasone free base. In some embodiments, the anti-inflammatory is bethamethasone valerate. In some embodiments, the anti-inflammatory is bethamethasone dipropionate.

In some embodiments, the composition comprises a first anti-inflammatory. In some embodiments, the first anti-inflammatory is hydrocortisone, alclometasone, clocortolone, desonide, bethamethasone, fluocinolone, or triamcinolone, or a pharmaceutically acceptable salt thereof. In exemplary embodiments, the first anti-inflammatory is hydrocortisone, fluocinolone, or triamcinolone, or a pharmaceutically acceptable salt thereof. In some embodiments, the first anti-inflammatory is low potency hydrocortisone or a pharmaceutically acceptable salt thereof.

In some embodiments, the first anti-inflammatory is hydrocortisone or a pharmaceutically acceptable salt thereof. In some embodiments, the hydrocortisone, or the pharmaceutically acceptable salt thereof, is in a crystalline form. In some embodiments, the first anti-inflammatory is hydrocortisone free alcohol. In some embodiments, the first anti-inflammatory is hydrocortisone acetate. In some embodiments, the first anti-inflammatory is hydrocortisone valerate. In some embodiments, the first anti-inflammatory is hydrocortisone sodium succinate. In some embodiments, the first anti-inflammatory is hydrocortisone butyrate.

In some embodiments, the first anti-inflammatory is fluocinolone or a pharmaceutically acceptable salt thereof. In some embodiments, the fluocinolone, or the pharmaceutically acceptable salt thereof, is in a crystalline form. In some embodiments, the first anti-inflammatory is fluocinolone free alcohol. In some embodiments, the first anti-inflammatory is fluocinolone acetonide.

In some embodiments, the first anti-inflammatory is triamcinolone or a pharmaceutically acceptable salt thereof. In some embodiments, the triamcinolone, or the pharmaceutically acceptable salt thereof, is in a crystalline form. In some embodiments, the first anti-inflammatory is triamcinolone free alcohol. In some embodiments, the first anti-inflammatory is triamcinolone acetonide. In some embodiments, the first anti-inflammatory is triamcinolone diacetate.

In some embodiments, the first anti-inflammatory is alclometasone or a pharmaceutically acceptable salt thereof. In some embodiments, the alclometasone, or the pharmaceutically acceptable salt thereof, is in a crystalline form. In some embodiments, the first anti-inflammatory is alclometasone free alcohol. In some embodiments, the first anti-inflammatory is alclometasone dipropionate.

In some embodiments, the first anti-inflammatory is clocortolone or a pharmaceutically acceptable salt thereof. In some embodiments, the clocortolone, or the pharmaceutically acceptable salt thereof, is in a crystalline form. In some embodiments, the first anti-inflammatory is clocortolone free alcohol. In some embodiments, the first anti-inflammatory is clocortolone pivalate.

In some embodiments, the first anti-inflammatory is bethamethasone or a pharmaceutically acceptable salt thereof. In some embodiments, the bethamethasone, or the pharmaceutically acceptable salt thereof, is in a crystalline form. In some embodiments, the first anti-inflammatory is bethamethasone free base. In some embodiments, the first anti-inflammatory is bethamethasone valerate. In some embodiments, the first anti-inflammatory is bethamethasone dipropionate.

In some embodiments, the composition contains the first anti-inflammatory in an amount between about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.35% v/v, about 0.01 and about 0.3% v/v, about 0.01 and about 0.25% v/v, about 0.01 and about 0.2% v/v, about 0.01 and about 0.15% v/v, about 0.01 and about 0.1% v/v, about 0.01 and about 0.05% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.35% v/v, about 0.05 and about 0.3% v/v, about 0.05 and about 0.25% v/v, about 0.05 and about 0.2% v/v, about 0.05 and about 0.15% v/v, about 0.05 and about 0.1% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.35% v/v, about 0.1 and about 0.3% v/v, about 0.1 and about 0.25% v/v, about 0.1 and about 0.2% v/v, about 0.1 and about 0.15% v/v, about 0.15 and about 2% v/v, about 0.15 and about 1% v/v, about 0.15 and about 0.75% v/v, about 0.15 and about 0.6% v/v, about 0.15 and about 0.5% v/v, about 0.15 and about 0.4% v/v, about 0.15 and about 0.35% v/v, about 0.15 and about 0.3% v/v, about 0.15 and about 0.25% v/v, about 0.15 and about 0.2% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.35% v/v, about 0.2 and about 0.3% v/v, about 0.2 and about 0.25% v/v, about 0.25 and about 2% v/v, about 0.25 and about 1% v/v, about 0.25 and about 0.75% v/v, about 0.25 and about 0.6% v/v, about 0.25 and about 0.5% v/v, about 0.25 and about 0.4% v/v, about 0.25 and about 0.35% v/v, about 0.25 and about 0.3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.3 and about 0.35% v/v, about 0.35 and about 2% v/v, about 0.35 and about 1% v/v, about 0.35 and about 0.75% v/v, about 0.35 and about 0.6% v/v, about 0.35 and about 0.5% v/v, about 0.35 and about 0.4% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 2% v/v, about 0.5 and about 1% v/v, about 0.5 and about 0.75% v/v, about 0.5 and about 0.6% v/v, about 0.6 and about 2% v/v, about 0.6 and about 1% v/v, about 0.6 and about 0.75% v/v, about 0.75 and about 2% v/v, about 0.75 and about 1% v/v, or about 1 and about 2% v/v.

In exemplary embodiments, the composition contains the first anti-inflammatory in an amount of about 0.01% v/v, about 0.05% v/v, about 0.1% v/v, about 0.15% v/v, about 0.2% v/v, about 0.25% v/v, about 0.3% v/v, about 0.35% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first anti-inflammatory in an amount between about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.35% w/w, about 0.01 and about 0.3% w/w, about 0.01 and about 0.25% w/w, about 0.01 and about 0.2% w/w, about 0.01 and about 0.15% w/w, about 0.01 and about 0.1% w/w, about 0.01 and about 0.05% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.35% w/w, about 0.05 and about 0.3% w/w, about 0.05 and about 0.25% w/w, about 0.05 and about 0.2% w/w, about 0.05 and about 0.15% w/w, about 0.05 and about 0.1% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.35% w/w, about 0.1 and about 0.3% w/w, about 0.1 and about 0.25% w/w, about 0.1 and about 0.2% w/w, about 0.1 and about 0.15% w/w, about 0.15 and about 2% w/w, about 0.15 and about 1% w/w, about 0.15 and about 0.75% w/w, about 0.15 and about 0.6% w/w, about 0.15 and about 0.5% w/w, about 0.15 and about 0.4% w/w, about 0.15 and about 0.35% w/w, about 0.15 and about 0.3% w/w, about 0.15 and about 0.25% w/w, about 0.15 and about 0.2% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.35% w/w, about 0.2 and about 0.3% w/w, about 0.2 and about 0.25% w/w, about 0.25 and about 2% w/w, about 0.25 and about 1% w/w, about 0.25 and about 0.75% w/w, about 0.25 and about 0.6% w/w, about 0.25 and about 0.5% w/w, about 0.25 and about 0.4% w/w, about 0.25 and about 0.35% w/w, about 0.25 and about 0.3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.3 and about 0.35% w/w, about 0.35 and about 2% w/w, about 0.35 and about 1% w/w, about 0.35 and about 0.75% w/w, about 0.35 and about 0.6% w/w, about 0.35 and about 0.5% w/w, about 0.35 and about 0.4% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 2% w/w, about 0.5 and about 1% w/w, about 0.5 and about 0.75% w/w, about 0.5 and about 0.6% w/w, about 0.6 and about 2% w/w, about 0.6 and about 1% w/w, about 0.6 and about 0.75% w/w, about 0.75 and about 2% w/w, about 0.75 and about 1% w/w, or about 1 and about 2% w/w.

In exemplary embodiments, the composition contains the first anti-inflammatory in an amount of about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the composition comprises a first anti-inflammatory and a second anti-inflammatory. In some embodiments, the first anti-inflammatory is different from the second anti-inflammatory. The second anti-inflammatory may be, but is not limited to, one of the anti-inflammatory agents previously described herein. The composition may contain the second anti-inflammatory in an amount previously described herein.

In some embodiments, the second anti-inflammatory is hydrocortisone, alclometasone, clocortolone, desonide, bethamethasone, fluocinolone, or triamcinolone, or a pharmaceutically acceptable salt thereof. In some embodiments, the second anti-inflammatory is hydrocortisone, fluocinolone, or triamcinolone, or a pharmaceutically acceptable salt thereof.

In some embodiments, the second anti-inflammatory is hydrocortisone or a pharmaceutically acceptable salt thereof. In some embodiments, the hydrocortisone, or the pharmaceutically acceptable salt thereof, is in a crystalline form. In some embodiments, the second anti-inflammatory is hydrocortisone free alcohol. In some embodiments, the second anti-inflammatory is hydrocortisone acetate. In some embodiments, the second anti-inflammatory is hydrocortisone valerate. In some embodiments, the second anti-inflammatory is hydrocortisone sodium succinate. In some embodiments, the second anti-inflammatory is hydrocortisone butyrate.

In some embodiments, the second anti-inflammatory is fluocinolone or a pharmaceutically acceptable salt thereof. In some embodiments, the fluocinolone, or the pharmaceutically acceptable salt thereof, is in a crystalline form. In some embodiments, the second anti-inflammatory is fluocinolone free alcohol. In some embodiments, the second anti-inflammatory is fluocinolone acetonide.

In some embodiments, the second anti-inflammatory is triamcinolone or a pharmaceutically acceptable salt thereof. In some embodiments, the triamcinolone, or the pharmaceutically acceptable salt thereof, is in a crystalline form. In some embodiments, the second anti-inflammatory is triamcinolone free alcohol. In some embodiments, the second anti-inflammatory is triamcinolone acetonide. In some embodiments, the second anti-inflammatory is triamcinolone diacetate.

In some embodiments, the second anti-inflammatory is alclometasone or a pharmaceutically acceptable salt thereof. In some embodiments, the alclometasone, or the pharmaceutically acceptable salt thereof, is in a crystalline form. In some embodiments, the second anti-inflammatory is alclometasone free alcohol. In some embodiments, the second anti-inflammatory is alclometasone dipropionate.

In some embodiments, the second anti-inflammatory is clocortolone or a pharmaceutically acceptable salt thereof. In some embodiments, the clocortolone, or the pharmaceutically acceptable salt thereof, is in a crystalline form. In some embodiments, the second anti-inflammatory is clocortolone free alcohol. In some embodiments, the second anti-inflammatory is clocortolone pivalate.

In some embodiments, the second anti-inflammatory is bethamethasone or a pharmaceutically acceptable salt thereof. In some embodiments, the bethamethasone, or the pharmaceutically acceptable salt thereof, is in a crystalline form. In some embodiments, the second anti-inflammatory is bethamethasone free base. In some embodiments, the second anti-inflammatory is bethamethasone valerate. In some embodiments, the second anti-inflammatory is bethamethasone dipropionate.

In some embodiments, the composition contains the second anti-inflammatory in an amount between about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.35% v/v, about 0.01 and about 0.3% v/v, about 0.01 and about 0.25% v/v, about 0.01 and about 0.2% v/v, about 0.01 and about 0.15% v/v, about 0.01 and about 0.1% v/v, about 0.01 and about 0.05% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.35% v/v, about 0.05 and about 0.3% v/v, about 0.05 and about 0.25% v/v, about 0.05 and about 0.2% v/v, about 0.05 and about 0.15% v/v, about 0.05 and about 0.1% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.35% v/v, about 0.1 and about 0.3% v/v, about 0.1 and about 0.25% v/v, about 0.1 and about 0.2% v/v, about 0.1 and about 0.15% v/v, about 0.15 and about 2% v/v, about 0.15 and about 1% v/v, about 0.15 and about 0.75% v/v, about 0.15 and about 0.6% v/v, about 0.15 and about 0.5% v/v, about 0.15 and about 0.4% v/v, about 0.15 and about 0.35% v/v, about 0.15 and about 0.3% v/v, about 0.15 and about 0.25% v/v, about 0.15 and about 0.2% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.35% v/v, about 0.2 and about 0.3% v/v, about 0.2 and about 0.25% v/v, about 0.25 and about 2% v/v, about 0.25 and about 1% v/v, about 0.25 and about 0.75% v/v, about 0.25 and about 0.6% v/v, about 0.25 and about 0.5% v/v, about 0.25 and about 0.4% v/v, about 0.25 and about 0.35% v/v, about 0.25 and about 0.3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.35% v/v, about 0.35 and about 2% v/v, about 0.35 and about 1% v/v, about 0.35 and about 0.75% v/v, about 0.35 and about 0.6% v/v, about 0.35 and about 0.5% v/v, about 0.35 and about 0.4% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 2% v/v, about 0.5 and about 1% v/v, about 0.5 and about 0.75% v/v, about 0.5 and about 0.6% v/v, about 0.6 and about 2% v/v, about 0.6 and about 1% v/v, about 0.6 and about 0.75% v/v, about 0.75 and about 2% v/v, about 0.75 and about 1% v/v, or about 1 and about 2% v/v.

In exemplary embodiments, the composition contains the second anti-inflammatory in an amount of about 0.01% v/v, about 0.05% v/v, about 0.1% v/v, about 0.15% v/v, about 0.2% v/v, about 0.25% v/v, about 0.3% v/v, about 0.35% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the second anti-inflammatory in an amount between about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.35% w/w, about 0.01 and about 0.3% w/w, about 0.01 and about 0.25% w/w, about 0.01 and about 0.2% w/w, about 0.01 and about 0.15% w/w, about 0.01 and about 0.1% w/w, about 0.01 and about 0.05% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.35% w/w, about 0.05 and about 0.3% w/w, about 0.05 and about 0.25% w/w, about 0.05 and about 0.2% w/w, about 0.05 and about 0.15% w/w, about 0.05 and about 0.1% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.35% w/w, about 0.1 and about 0.3% w/w, about 0.1 and about 0.25% w/w, about 0.1 and about 0.2% w/w, about 0.1 and about 0.15% w/w, about 0.15 and about 2% w/w, about 0.15 and about 1% w/w, about 0.15 and about 0.75% w/w, about 0.15 and about 0.6% w/w, about 0.15 and about 0.5% w/w, about 0.15 and about 0.4% w/w, about 0.15 and about 0.35% w/w, about 0.15 and about 0.3% w/w, about 0.15 and about 0.25% w/w, about 0.15 and about 0.2% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.35% w/w, about 0.2 and about 0.3% w/w, about 0.2 and about 0.25% w/w, about 0.25 and about 2% w/w, about 0.25 and about 1% w/w, about 0.25 and about 0.75% w/w, about 0.25 and about 0.6% w/w, about 0.25 and about 0.5% w/w, about 0.25 and about 0.4% w/w, about 0.25 and about 0.35% w/w, about 0.25 and about 0.3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.3 and about 0.35% w/w, about 0.35 and about 2% w/w, about 0.35 and about 1% w/w, about 0.35 and about 0.75% w/w, about 0.35 and about 0.6% w/w, about 0.35 and about 0.5% w/w, about 0.35 and about 0.4% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 2% w/w, about 0.5 and about 1% w/w, about 0.5 and about 0.75% w/w, about 0.5 and about 0.6% w/w, about 0.6 and about 2% w/w, about 0.6 and about 1% w/w, about 0.6 and about 0.75% w/w, about 0.75 and about 2% w/w, about 0.75 and about 1% w/w, or about 1 and about 2% w/w.

In exemplary embodiments, the composition contains the second anti-inflammatory in an amount of about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the first anti-inflammatory is hydrocortisone, or a pharmaceutically acceptable salt thereof, and the second anti-inflammatory is alclometasone, clocortolone, desonide, bethamethasone, fluocinolone, or triamcinolone, or a pharmaceutically acceptable salt thereof. In some embodiments, the hydrocortisone, or the pharmaceutically acceptable salt thereof, is in a crystalline form. In some embodiments, the first anti-inflammatory is hydrocortisone free alcohol and the second anti-inflammatory is alclometasone, clocortolone, desonide, bethamethasone, fluocinolone, or triamcinolone, or a pharmaceutically acceptable salt thereof. In some embodiments, the first anti-inflammatory is hydrocortisone acetate and the second anti-inflammatory is alclometasone, clocortolone, desonide, bethamethasone, fluocinolone, or triamcinolone, or a pharmaceutically acceptable salt thereof. In some embodiments, the first anti-inflammatory is hydrocortisone valerate and the second anti-inflammatory is alclometasone, clocortolone, desonide, bethamethasone, fluocinolone, or triamcinolone, or a pharmaceutically acceptable salt thereof. In some embodiments, the first anti-inflammatory is hydrocortisone sodium succinate and the second anti-inflammatory is alclometasone, clocortolone, desonide, bethamethasone, fluocinolone, or triamcinolone, or a pharmaceutically acceptable salt thereof. In some embodiments, the first anti-inflammatory is hydrocortisone butyrate and the second anti-inflammatory is alclometasone, clocortolone, desonide, bethamethasone, fluocinolone, or triamcinolone, or a pharmaceutically acceptable salt thereof, the first anti-inflammatory In some embodiments, the first anti-inflammatory is fluocinolone, or a pharmaceutically acceptable salt thereof, and the second anti-inflammatory is hydrocortisone, alclometasone, clocortolone, desonide, bethamethasone, or triamcinolone, or a pharmaceutically acceptable salt thereof. In some embodiments, the fluocinolone, or the pharmaceutically acceptable salt thereof, is in a crystalline form. In some embodiments, the first anti-inflammatory is fluocinolone free alcohol and the second anti-inflammatory is hydrocortisone, alclometasone, clocortolone, desonide, bethamethasone, or triamcinolone, or a pharmaceutically acceptable salt thereof. In some embodiments, the first anti-inflammatory is fluocinolone acetonide and the second anti-inflammatory is alclometasone, clocortolone, desonide, bethamethasone, or triamcinolone, or a pharmaceutically acceptable salt thereof. the first anti-inflammatory In some embodiments, the first anti-inflammatory is triamcinolone, or a pharmaceutically acceptable salt thereof, and the second anti-inflammatory is hydrocortisone, alclometasone, clocortolone, desonide, bethamethasone, or fluocinolone, or a pharmaceutically acceptable salt thereof. In some embodiments, the triamcinolone, or the pharmaceutically acceptable salt thereof, is in a crystalline form. In some embodiments, the first anti-inflammatory is triamcinolone free alcohol and the second anti-inflammatory is hydrocortisone, alclometasone, clocortolone, desonide, bethamethasone, or fluocinolone, or a pharmaceutically acceptable salt thereof. In some embodiments, the first anti-inflammatory is triamcinolone acetonide and the second anti-inflammatory is alclometasone, clocortolone, desonide, bethamethasone, or fluocinolone, or a pharmaceutically acceptable salt thereof. In some embodiments, the first anti-inflammatory is triamcinolone diacetate and the second anti-inflammatory is alclometasone, clocortolone, desonide, bethamethasone, or fluocinolone, or a pharmaceutically acceptable salt thereof. the first anti-inflammatory In some embodiments, the composition contains the first anti-inflammatory and the second anti-inflammatory in a combined amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the first anti-inflammatory and the second anti-inflammatory in a combined amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first anti-inflammatory and the second anti-inflammatory in a combined amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the first anti-inflammatory and the second anti-inflammatory in a combined amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the composition comprises a first anti-inflammatory, a second anti-inflammatory, and a third anti-inflammatory. In some embodiments, the first anti-inflammatory, the second anti-inflammatory, and the third anti-inflammatory are each different from each other. The third anti-inflammatory may be, but is not limited to, one of the anti-inflammatory agents previously described herein. The composition may contain the third anti-inflammatory in an amount previously described herein.

In some embodiments, the composition comprises a first anti-inflammatory, a second anti-inflammatory, a third anti-inflammatory, and a fourth anti-inflammatory. In some embodiments, the first anti-inflammatory, the second anti-inflammatory, the third anti-inflammatory, and the fourth anti-inflammatory are each different from each other. The fourth anti-inflammatory may be, but is not limited to, one of the anti-inflammatory agents previously described herein. The composition may contain the fourth anti-inflammatory in an amount previously described herein.

In some embodiments, the composition contains the first anti-inflammatory, the second anti-inflammatory, and the third anti-inflammatory, or the first anti-inflammatory, the second anti-inflammatory, the third anti-inflammatory, and the fourth anti-inflammatory, in a combined amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In exemplary embodiments, the composition contains the first anti-inflammatory, the second anti-inflammatory, and the third anti-inflammatory, or the first anti-inflammatory, the second anti-inflammatory, the third anti-inflammatory, and the fourth anti-inflammatory, in a combined amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the first anti-inflammatory, the second anti-inflammatory, and the third anti-inflammatory, or the first anti-inflammatory, the second anti-inflammatory, the third anti-inflammatory, and the fourth anti-inflammatory, in a combined amount between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In exemplary embodiments, the composition contains the first anti-inflammatory, the second anti-inflammatory, and the third anti-inflammatory, or the first anti-inflammatory, the second anti-inflammatory, the third anti-inflammatory, and the fourth anti-inflammatory, in a combined amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

D. Relative Amounts of Components

In some embodiments, the composition comprises one or more of an antifungal, an antibacterial, and an anti-inflammatory. In some embodiments, the composition comprises two or more of an antifungal, an antibacterial, and an anti-inflammatory. In some embodiments, the composition comprises an antifungal, an antibacterial, and an anti-inflammatory. In some embodiments, the composition consists essentially of an antifungal, an antibacterial, and an anti-inflammatory. In some embodiments, the composition contains two or three of the antifungal, the antibacterial, and the anti-inflammatory in equal amounts v/v. In some embodiments, the composition contains two or three of the antifungal, the antibacterial, and the anti-inflammatory in equal amounts w/w.

In some embodiments, the composition comprises a first antifungal, a second antifungal, a first antibacterial, and a first anti-inflammatory. In some embodiments, the composition consists essentially of a first antifungal, a second antifungal, a first antibacterial, and a first anti-inflammatory. In some embodiments, the composition contains two, three, or four of the first antifungal, the second antifungal, the first antibacterial, and the first anti-inflammatory in equal amounts v/v. In some embodiments, the composition contains two, three, or four of the first antifungal, the second antifungal, the first antibacterial, and the first anti-inflammatory in equal amounts w/w.

In some embodiments, the composition comprises a first antifungal, a second antifungal, a first antibacterial, a second antibacterial, and a first anti-inflammatory. In some embodiments, the composition consists essentially of a first antifungal, a second antifungal, a first antibacterial, a second antibacterial, and a first anti-inflammatory. In some embodiments, the composition contains two, three, four, or five of the first antifungal the first antifungal, the second antifungal, the first antibacterial, the second antibacterial, and the first anti-inflammatory in equal amounts v/v. In some embodiments, the composition contains two, three, four, or five of the first antifungal the first antifungal, the second antifungal, the first antibacterial, the second antibacterial, and the first anti-inflammatory in equal amounts w/w.

In some embodiments, the composition comprises a first antifungal, a second antifungal, a first antibacterial, a first anti-inflammatory, and a second anti-inflammatory. In some embodiments, the composition consists essentially of a first antifungal, a second antifungal, a first antibacterial, a first anti-inflammatory, and a second anti-inflammatory. In some embodiments, the composition contains two, three, four, or five of the first antifungal the first antifungal, the second antifungal, the first antibacterial, the first anti-inflammatory, and the second anti-inflammatory in equal amounts v/v. In some embodiments, the composition contains two, three, four, or five of the first antifungal, the second antifungal, the first antibacterial, the first anti-inflammatory, and the second anti-inflammatory in equal amounts w/w.

In some embodiments, the composition comprises a first antifungal, a second antifungal, a first antibacterial, a second antibacterial, a first anti-inflammatory, and a second anti-inflammatory. In some embodiments, the composition consists essentially of a first antifungal, a second antifungal, a first antibacterial, a second antibacterial, a first anti-inflammatory, and a second anti-inflammatory. In some embodiments, the composition contains two, three, four, five, or six of the first antifungal, the second antifungal, the first antibacterial, the second antibacterial, the first anti-inflammatory, and the second anti-inflammatory in equal amounts v/v. In some embodiments, the composition contains two, three, four, five, or six of the first antifungal, the second antifungal, the first antibacterial, the second antibacterial, the first anti-inflammatory, and the second anti-inflammatory in equal amounts w/w.

In some embodiments, the composition comprises a first antifungal, a first antibacterial, a second antibacterial, and a first anti-inflammatory. In some embodiments, the composition consists essentially of a first antifungal, a first antibacterial, a second antibacterial, and a first anti-inflammatory. In some embodiments, the composition contains two, three, or four of the first antifungal, the first antibacterial, the second antibacterial, and the first anti-inflammatory in equal amounts v/v. In some embodiments, the composition contains two, three, or four of the first antifungal, the first antibacterial, the second antibacterial, and the first anti-inflammatory in equal amounts w/w.

In some embodiments, the composition comprises a first antifungal, a first antibacterial, a first anti-inflammatory, and a second anti-inflammatory. In some embodiments, the composition consists essentially of a first antifungal, a first antibacterial, a first anti-inflammatory, and a second anti-inflammatory. In some embodiments, the composition contains two, three, or four of the first antifungal, the first antibacterial, the first anti-inflammatory, and the second anti-inflammatory in equal amounts v/v. In some embodiments, the composition contains two, three, or four of the first antifungal, the first antibacterial, the first anti-inflammatory, and the second anti-inflammatory in equal amounts w/w.

In some embodiments, the composition comprises a first antifungal, a first antibacterial, a second antibacterial, a first anti-inflammatory, and a second anti-inflammatory. In some embodiments, the composition consists essentially of a first antifungal, a first antibacterial, a second antibacterial, a first anti-inflammatory, and a second anti-inflammatory. In some embodiments, the composition contains two, three, four, or five of the first antifungal, the first antibacterial, the second antibacterial, the first anti-inflammatory, and the second anti-inflammatory in equal amounts v/v. In some embodiments, the composition contains two, three, four, or five of the first antifungal, the first antibacterial, the second antibacterial, the first anti-inflammatory, and the second anti-inflammatory in equal amounts w/w.

In some embodiments, the composition comprises about 0.05% to about 1.0% v/v of a first antifungal, about 0.05% to about 1.0% v/v of a first antibacterial, and about 0.05% to about 1.0% v/v of a first anti-inflammatory. In some embodiments, the composition consists essentially of about 0.05% to about 1.0% v/v of a first antifungal, about 0.05% to about 1.0% v/v of a first antibacterial, and about 0.05% to about 1.0% v/v of a first anti-inflammatory. In some embodiments, the composition comprises about 0.05% to about 1.0% w/w of a first antifungal, about 0.05% to about 1.0% w/w of a first antibacterial, and about 0.05% to about 1.0% w/w of a first anti-inflammatory. In some embodiments, the composition consists essentially of about 0.05% to about 1.0% w/w of a first antifungal, about 0.05% to about 1.0% w/w of a first antibacterial, and about 0.05% to about 1.0% w/w of a first anti-inflammatory.

In some embodiments, the composition comprises about 0.05% to about 1.0% v/v of a first antifungal, about 0.05% to about 1.0% v/v of a second antifungal, about 0.05% to about 1.0% v/v of a first antibacterial, and about 0.05% to about 1.0% v/v of a first anti-inflammatory. In some embodiments, the composition consists essentially of about 0.05% to about 1.0% v/v of a first antifungal, about 0.05% to about 1.0% v/v of a second antifungal, about 0.05% to about 1.0% v/v of a first antibacterial, and about 0.05% to about 1.0% v/v of a first anti-inflammatory. In some embodiments, the composition comprises about 0.2% to about 0.3% v/v of a first antifungal, about 0.2% to about 0.3% v/v of a second antifungal, about 0.4% to about 0.6% v/v of a first antibacterial, and about 0.2% to about 0.3% v/v of a first anti-inflammatory. In some embodiments, the composition consists essentially of about 0.2% to about 0.3% v/v of a first antifungal, about 0.2% to about 0.3% v/v of a second antifungal, about 0.4% to about 0.6% v/v of a first antibacterial, and about 0.2% to about 0.3% v/v of a first anti-inflammatory. In some embodiments, the composition comprises about 0.25% v/v of a first antifungal, about 0.25% v/v of a second antifungal, about 0.5% v/v of a first antibacterial, and about 0.25% v/v of a first anti-inflammatory. In some embodiments, the composition consists essentially of about 0.25% v/v of a first antifungal, about 0.25% v/v of a second antifungal, about 0.5% v/v of a first antibacterial, and about 0.25% v/v of a first anti-inflammatory.

In some embodiments, the composition comprises about 0.05% to about 1.0% w/w of a first antifungal, about 0.05% to about 1.0% w/w of a second antifungal, about 0.05% to about 1.0% w/w of a first antibacterial, and about 0.05% to about 1.0% w/w of a first anti-inflammatory. In some embodiments, the composition consists essentially of about 0.05% to about 1.0% w/w of a first antifungal, about 0.05% to about 1.0% w/w of a second antifungal, about 0.05% to about 1.0% w/w of a first antibacterial, and about 0.05% to about 1.0% w/w of a first anti-inflammatory. In some embodiments, the composition comprises about 0.2% to about 0.3% w/w of a first antifungal, about 0.2% to about 0.3% w/w of a second antifungal, about 0.4% to about 0.6% w/w of a first antibacterial, and about 0.2% to about 0.3% w/w of a first anti-inflammatory. In some embodiments, the composition consists essentially of about 0.2% to about 0.3% w/w of a first antifungal, about 0.2% to about 0.3% w/w of a second antifungal, about 0.4% to about 0.6% w/w of a first antibacterial, and about 0.2% to about 0.3% w/w of a first anti-inflammatory. In some embodiments, the composition comprises about 0.25% w/w of a first antifungal, about 0.25% w/w of a second antifungal, about 0.5% w/w of a first antibacterial, and about 0.25% w/w of a first anti-inflammatory. In some embodiments, the composition consists essentially of about 0.25% w/w of a first antifungal, about 0.25% w/w of a second antifungal, about 0.5% w/w of a first antibacterial, and about 0.25% w/w of a first anti-inflammatory.

In some embodiments, the composition comprises about 0.05% to about 1.0% v/v of clotrimazole or nystatin, or a pharmaceutically acceptable salt thereof, about 0.05% to about 1.0% v/v of terbinafine or nystatin, or a pharmaceutically acceptable salt thereof, about 0.05% to about 1.0% v/v of mupirocin or bacitracin, or a pharmaceutically acceptable salt thereof, and about 0.05% to about 1.0% v/v of hydrocortisone or triamcinolone, or a pharmaceutically acceptable salt thereof. In some embodiments, the composition consists essentially of about 0.05% to about 1.0% v/v of clotrimazole or nystatin, or a pharmaceutically acceptable salt thereof, about 0.05% to about 1.0% v/v of terbinafine or nystatin, or a pharmaceutically acceptable salt thereof, about 0.05% to about 1.0% v/v of mupirocin or bacitracin, or a pharmaceutically acceptable salt thereof, and about 0.05% to about 1.0% v/v of hydrocortisone or triamcinolone, or a pharmaceutically acceptable salt thereof. In some embodiments, the composition comprises about 0.2% to about 0.3% v/v of clotrimazole or nystatin, or a pharmaceutically acceptable salt thereof, about 0.2% to about 0.3% v/v of terbinafine or nystatin, or a pharmaceutically acceptable salt thereof, about 0.4% to about 0.6% v/v of mupirocin or bacitracin, or a pharmaceutically acceptable salt thereof, and about 0.2% to about 0.3% v/v of hydrocortisone or triamcinolone, or a pharmaceutically acceptable salt thereof. In some embodiments, the composition consists essentially of about 0.2% to about 0.3% v/v of clotrimazole or nystatin, or a pharmaceutically acceptable salt thereof, about 0.2% to about 0.3% v/v of terbinafine or nystatin, or a pharmaceutically acceptable salt thereof, about 0.4% to about 0.6% v/v of mupirocin or bacitracin, or a pharmaceutically acceptable salt thereof, and about 0.2% to about 0.3% v/v of hydrocortisone or triamcinolone, or a pharmaceutically acceptable salt thereof. In some embodiments, the composition comprises about 0.25% v/v of clotrimazole or nystatin, or a pharmaceutically acceptable salt thereof, about 0.25% v/v of terbinafine or nystatin, or a pharmaceutically acceptable salt thereof, about 0.5% v/v of mupirocin or bacitracin, or a pharmaceutically acceptable salt thereof, and about 0.25% v/v of hydrocortisone or triamcinolone, or a pharmaceutically acceptable salt thereof. In some embodiments, the composition consists essentially of about 0.25% v/v of clotrimazole or nystatin, or a pharmaceutically acceptable salt thereof, about 0.25% v/v of terbinafine or nystatin, or a pharmaceutically acceptable salt thereof, about 0.5% v/v of mupirocin or bacitracin, or a pharmaceutically acceptable salt thereof, and about 0.25% v/v of hydrocortisone or triamcinolone, or a pharmaceutically acceptable salt thereof.

In some embodiments, the composition comprises about 0.05% to about 1.0% w/w of clotrimazole or nystatin, or a pharmaceutically acceptable salt thereof, about 0.05% to about 1.0% w/w of terbinafine or nystatin, or a pharmaceutically acceptable salt thereof, about 0.05% to about 1.0% w/w of mupirocin or bacitracin, or a pharmaceutically acceptable salt thereof, and about 0.05% to about 1.0% w/w of hydrocortisone or triamcinolone, or a pharmaceutically acceptable salt thereof. In some embodiments, the composition consists essentially of about 0.05% to about 1.0% w/w of clotrimazole or nystatin, or a pharmaceutically acceptable salt thereof, about 0.05% to about 1.0% w/w of terbinafine or nystatin, or a pharmaceutically acceptable salt thereof, about 0.05% to about 1.0% w/w of mupirocin or bacitracin, or a pharmaceutically acceptable salt thereof, and about 0.05% to about 1.0% w/w of hydrocortisone or triamcinolone, or a pharmaceutically acceptable salt thereof. In some embodiments, the composition comprises about 0.2% to about 0.3% w/w of clotrimazole or nystatin, or a pharmaceutically acceptable salt thereof, about 0.2% to about 0.3% w/w of terbinafine or nystatin, or a pharmaceutically acceptable salt thereof, about 0.4% to about 0.6% w/w of mupirocin or bacitracin, or a pharmaceutically acceptable salt thereof, and about 0.2% to about 0.3% w/w of hydrocortisone or triamcinolone, or a pharmaceutically acceptable salt thereof. In some embodiments, the composition consists essentially of about 0.2% to about 0.3% w/w of clotrimazole or nystatin, or a pharmaceutically acceptable salt thereof, about 0.2% to about 0.3% w/w of terbinafine or nystatin, or a pharmaceutically acceptable salt thereof, about 0.4% to about 0.6% w/w of mupirocin or bacitracin, or a pharmaceutically acceptable salt thereof, and about 0.2% to about 0.3% w/w of hydrocortisone or triamcinolone, or a pharmaceutically acceptable salt thereof. In some embodiments, the composition comprises about 0.25% w/w of clotrimazole or nystatin, or a pharmaceutically acceptable salt thereof, about 0.25% w/w of terbinafine or nystatin, or a pharmaceutically acceptable salt thereof, about 0.5% w/w of mupirocin or bacitracin, or a pharmaceutically acceptable salt thereof, and about 0.25% w/w of hydrocortisone or triamcinolone, or a pharmaceutically acceptable salt thereof. In some embodiments, the composition consists essentially of about 0.25% w/w of clotrimazole or nystatin, or a pharmaceutically acceptable salt thereof, about 0.25% w/w of terbinafine or nystatin, or a pharmaceutically acceptable salt thereof, about 0.5% w/w of mupirocin or bacitracin, or a pharmaceutically acceptable salt thereof, and about 0.25% w/w of hydrocortisone or triamcinolone, or a pharmaceutically acceptable salt thereof.

In some embodiments, the composition comprises about 0.05% to about 1.0% v/v of clotrimazole or a pharmaceutically acceptable salt thereof, about 0.05% to about 1.0% v/v of terbinafine or a pharmaceutically acceptable salt thereof, about 0.05% to about 1.0% v/v of mupirocin or a pharmaceutically acceptable salt thereof, and about 0.05% to about 1.0% v/v of hydrocortisone or a pharmaceutically acceptable salt thereof. In some embodiments, the composition consists essentially of about 0.05% to about 1.0% v/v of clotrimazole or a pharmaceutically acceptable salt thereof, about 0.05% to about 1.0% v/v of terbinafine or a pharmaceutically acceptable salt thereof, about 0.05% to about 1.0% v/v of mupirocin or a pharmaceutically acceptable salt thereof, and about 0.05% to about 1.0% v/v of hydrocortisone or a pharmaceutically acceptable salt thereof. In some embodiments, the composition comprises about 0.2% to about 0.3% v/v of clotrimazole or a pharmaceutically acceptable salt thereof, about 0.2% to about 0.3% v/v of terbinafine or a pharmaceutically acceptable salt thereof, about 0.4% to about 0.6% v/v of mupirocin or a pharmaceutically acceptable salt thereof, and about 0.2% to about 0.3% v/v of hydrocortisone or a pharmaceutically acceptable salt thereof. In some embodiments, the composition consists essentially of about 0.2% to about 0.3% v/v of clotrimazole or a pharmaceutically acceptable salt thereof, about 0.2% to about 0.3% v/v of terbinafine or a pharmaceutically acceptable salt thereof, about 0.4% to about 0.6% v/v of mupirocin or a pharmaceutically acceptable salt thereof, and about 0.2% to about 0.3% v/v of hydrocortisone or a pharmaceutically acceptable salt thereof. In some embodiments, the composition comprises about 0.25% v/v of clotrimazole or a pharmaceutically acceptable salt thereof, about 0.25% v/v of terbinafine or a pharmaceutically acceptable salt thereof, about 0.5% v/v of mupirocin or a pharmaceutically acceptable salt thereof, and about 0.25% v/v of hydrocortisone or a pharmaceutically acceptable salt thereof. In some embodiments, the composition consists essentially of about 0.25% v/v of clotrimazole or a pharmaceutically acceptable salt thereof, about 0.25% v/v of terbinafine or a pharmaceutically acceptable salt thereof, about 0.5% v/v of mupirocin or a pharmaceutically acceptable salt thereof, and about 0.25% v/v of hydrocortisone or a pharmaceutically acceptable salt thereof.

In some embodiments, the composition comprises about 0.05% to about 1.0% w/w of clotrimazole or a pharmaceutically acceptable salt thereof, about 0.05% to about 1.0% w/w of terbinafine or a pharmaceutically acceptable salt thereof, about 0.05% to about 1.0% w/w of mupirocin or a pharmaceutically acceptable salt thereof, and about 0.05% to about 1.0% w/w of hydrocortisone or a pharmaceutically acceptable salt thereof. In some embodiments, the composition consists essentially of about 0.05% to about 1.0% w/w of clotrimazole or a pharmaceutically acceptable salt thereof, about 0.05% to about 1.0% w/w of terbinafine or a pharmaceutically acceptable salt thereof, about 0.05% to about 1.0% w/w of mupirocin or a pharmaceutically acceptable salt thereof, and about 0.05% to about 1.0% w/w of hydrocortisone or a pharmaceutically acceptable salt thereof. In some embodiments, the composition comprises about 0.2% to about 0.3% w/w of clotrimazole or a pharmaceutically acceptable salt thereof, about 0.2% to about 0.3% w/w of terbinafine or a pharmaceutically acceptable salt thereof, about 0.4% to about 0.6% w/w of mupirocin or a pharmaceutically acceptable salt thereof, and about 0.2% to about 0.3% w/w of hydrocortisone or a pharmaceutically acceptable salt thereof. In some embodiments, the composition consists essentially of about 0.2% to about 0.3% w/w of clotrimazole or a pharmaceutically acceptable salt thereof, about 0.2% to about 0.3% w/w of terbinafine or a pharmaceutically acceptable salt thereof, about 0.4% to about 0.6% w/w of mupirocin or a pharmaceutically acceptable salt thereof, and about 0.2% to about 0.3% w/w of hydrocortisone or a pharmaceutically acceptable salt thereof. In some embodiments, the composition comprises about 0.25% w/w of clotrimazole or a pharmaceutically acceptable salt thereof, about 0.25% w/w of terbinafine or a pharmaceutically acceptable salt thereof, about 0.5% w/w of mupirocin or a pharmaceutically acceptable salt thereof, and about 0.25% w/w of hydrocortisone or a pharmaceutically acceptable salt thereof. In some embodiments, the composition consists essentially of about 0.25% w/w of clotrimazole or a pharmaceutically acceptable salt thereof, about 0.25% w/w of terbinafine or a pharmaceutically acceptable salt thereof, about 0.5% w/w of mupirocin or a pharmaceutically acceptable salt thereof, and about 0.25% v/v of hydrocortisone or a pharmaceutically acceptable salt thereof.

E. Additional Components

In some embodiments, the topical formulation composition further includes one or more additional components. In some embodiments, the additional component is an additional active agent (i.e., an active agent that is not an antibacterial, an antifungal, or an anti-inflammatory). For example, the additional component may be, but is not limited to, an antiviral, an antihistamine, an anesthetic, an emollient, a keratolytic, or a rubefacient. In some embodiments, the composition comprises one or more active agents selected from the group consisting of an antiviral, an antihistamine, an anesthetic, an emollient, a keratolytic, or a rubefacient.

In some embodiments, the composition contains the additional active agent in an amount between about 0.01 and about 5% v/v, about 0.01 and about 4% v/v, about 0.01 and about 3% v/v, about 0.01 and about 2% v/v, about 0.01 and about 1% v/v, about 0.01 and about 0.75% v/v, about 0.01 and about 0.6% v/v, about 0.01 and about 0.5% v/v, about 0.01 and about 0.4% v/v, about 0.01 and about 0.3% v/v, about 0.01 and about 0.2% v/v, about 0.01 and about 0.1% v/v, about 0.01 and about 0.05% v/v, about 0.05 and about 5% v/v, about 0.05 and about 4% v/v, about 0.05 and about 3% v/v, about 0.05 and about 2% v/v, about 0.05 and about 1% v/v, about 0.05 and about 0.75% v/v, about 0.05 and about 0.6% v/v, about 0.05 and about 0.5% v/v, about 0.05 and about 0.4% v/v, about 0.05 and about 0.3% v/v, about 0.05 and about 0.2% v/v, about 0.05 and about 0.1% v/v, about 0.1 and about 5% v/v, about 0.1 and about 4% v/v, about 0.1 and about 3% v/v, about 0.1 and about 2% v/v, about 0.1 and about 1% v/v, about 0.1 and about 0.75% v/v, about 0.1 and about 0.6% v/v, about 0.1 and about 0.5% v/v, about 0.1 and about 0.4% v/v, about 0.1 and about 0.3% v/v, about 0.1 and about 0.2% v/v, about 0.2 and about 5% v/v, about 0.2 and about 4% v/v, about 0.2 and about 3% v/v, about 0.2 and about 2% v/v, about 0.2 and about 1% v/v, about 0.2 and about 0.75% v/v, about 0.2 and about 0.6% v/v, about 0.2 and about 0.5% v/v, about 0.2 and about 0.4% v/v, about 0.2 and about 0.3% v/v, about 0.3 and about 5% v/v, about 0.3 and about 4% v/v, about 0.3 and about 3% v/v, about 0.3 and about 2% v/v, about 0.3 and about 1% v/v, about 0.3 and about 0.75% v/v, about 0.3 and about 0.6% v/v, about 0.3 and about 0.5% v/v, about 0.3 and about 0.4% v/v, about 0.4 and about 5% v/v, about 0.4 and about 4% v/v, about 0.4 and about 3% v/v, about 0.4 and about 2% v/v, about 0.4 and about 1% v/v, about 0.4 and about 0.75% v/v, about 0.4 and about 0.6% v/v, about 0.4 and about 0.5% v/v, about 0.5 and about 5% v/v, about 0.5 and about 4% v/v, about 0.5 and about 3% v/v, about 0.5 and about 2% v/v, about 0.5 and about 1% v/v, about 0.5 and about 0.75% v/v, about 0.5 and about 0.6% v/v, about 0.6 and about 5% v/v, about 0.6 and about 4% v/v, about 0.6 and about 3% v/v, about 0.6 and about 2% v/v, about 0.6 and about 1% v/v, about 0.6 and about 0.75% v/v, about 0.75 and about 5% v/v, about 0.75 and about 4% v/v, about 0.75 and about 3% v/v, about 0.75 and about 2% v/v, about 0.75 and about 1% v/v, about 1 and about 5% v/v, about 1 and about 4% v/v, about 1 and about 3% v/v, about 1 and about 2% v/v, about 2 and about 5% v/v, about 2 and about 4% v/v, about 2 and about 3% v/v, about 3 and about 5% v/v, about 3 and about 4% v/v, or about 4 and about 5% v/v.

In some embodiments, the composition contains the additional active agent in an amount of about 0.01% v/v, about 0.05% v/v, about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 2% v/v, about 3% v/v, about 4% v/v, or about 5% v/v.

In some embodiments, the composition contains the additional active agent in an amount of between about 0.01 and about 5% w/w, about 0.01 and about 4% w/w, about 0.01 and about 3% w/w, about 0.01 and about 2% w/w, about 0.01 and about 1% w/w, about 0.01 and about 0.75% w/w, about 0.01 and about 0.6% w/w, about 0.01 and about 0.5% w/w, about 0.01 and about 0.4% w/w, about 0.01 and about 0.3% w/w, about 0.01 and about 0.2% w/w, about 0.01 and about 0.1% w/w, about 0.01 and about 0.05% w/w, about 0.05 and about 5% w/w, about 0.05 and about 4% w/w, about 0.05 and about 3% w/w, about 0.05 and about 2% w/w, about 0.05 and about 1% w/w, about 0.05 and about 0.75% w/w, about 0.05 and about 0.6% w/w, about 0.05 and about 0.5% w/w, about 0.05 and about 0.4% w/w, about 0.05 and about 0.3% w/w, about 0.05 and about 0.2% w/w, about 0.05 and about 0.1% w/w, about 0.1 and about 5% w/w, about 0.1 and about 4% w/w, about 0.1 and about 3% w/w, about 0.1 and about 2% w/w, about 0.1 and about 1% w/w, about 0.1 and about 0.75% w/w, about 0.1 and about 0.6% w/w, about 0.1 and about 0.5% w/w, about 0.1 and about 0.4% w/w, about 0.1 and about 0.3% w/w, about 0.1 and about 0.2% w/w, about 0.2 and about 5% w/w, about 0.2 and about 4% w/w, about 0.2 and about 3% w/w, about 0.2 and about 2% w/w, about 0.2 and about 1% w/w, about 0.2 and about 0.75% w/w, about 0.2 and about 0.6% w/w, about 0.2 and about 0.5% w/w, about 0.2 and about 0.4% w/w, about 0.2 and about 0.3% w/w, about 0.3 and about 5% w/w, about 0.3 and about 4% w/w, about 0.3 and about 3% w/w, about 0.3 and about 2% w/w, about 0.3 and about 1% w/w, about 0.3 and about 0.75% w/w, about 0.3 and about 0.6% w/w, about 0.3 and about 0.5% w/w, about 0.3 and about 0.4% w/w, about 0.4 and about 5% w/w, about 0.4 and about 4% w/w, about 0.4 and about 3% w/w, about 0.4 and about 2% w/w, about 0.4 and about 1% w/w, about 0.4 and about 0.75% w/w, about 0.4 and about 0.6% w/w, about 0.4 and about 0.5% w/w, about 0.5 and about 5% w/w, about 0.5 and about 4% w/w, about 0.5 and about 3% w/w, about 0.5 and about 2% w/w, about 0.5 and about 1% w/w, about 0.5 and about 0.75% w/w, about 0.5 and about 0.6% w/w, about 0.6 and about 5% w/w, about 0.6 and about 4% w/w, about 0.6 and about 3% w/w, about 0.6 and about 2% w/w, about 0.6 and about 1% w/w, about 0.6 and about 0.75% w/w, about 0.75 and about 5% w/w, about 0.75 and about 4% w/w, about 0.75 and about 3% w/w, about 0.75 and about 2% w/w, about 0.75 and about 1% w/w, about 1 and about 5% w/w, about 1 and about 4% w/w, about 1 and about 3% w/w, about 1 and about 2% w/w, about 2 and about 5% w/w, about 2 and about 4% w/w, about 2 and about 3% w/w, about 3 and about 5% w/w, about 3 and about 4% w/w, or about 4 and about 5% w/w.

In some embodiments, the composition contains the additional active agent in an amount of about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, or about 5% w/w.

In some embodiments, the additional component is a pharmaceutically acceptable excipient. As used herein, an "excipient" is a component of the composition that is not an active agent. In some embodiments, excipients are included in combinations and amounts that optimize the efficacy of the compositions. Excipients may include various organic or inorganic excipients or carrier substances, including, but not limited to, one or more solvents, preservatives, lubricants, binders, emulsifiers and surfactants, pH adjusters, and disintegrants. Excipients for use in the compositions of the present disclosure may include, but are not limited to, purified water, ethyl alcohol, benzyl alcohol, cetyl alcohol, stearyl alcohol, cetostearyl alcohol, cetyl alcohol, octyldodecanol, cetyl palmitate, isopropyl myristate, polysorbate 60, sodium hydroxide, sodium monostearate, glyceryl monostearate, corn oil, chamomile flower oil, mineral oil, paraffin, petrolatum, maltodextrin, phenoxyethanol, polyoxyl 20 cetostearyl ether, xanthan gum, methylparaben, propylene glycol, propylparaben, sodium lauryl sulfate, sodium cetostearyl sulfate, aloe vera gel, glycerin, citric acid, vitamin A palmitate, cholecalciferol, alpha-tocopherol acetate, and the like.

In some embodiments, the composition contains an excipient in an amount between about 0.01 and about 95% v/v, about 0.01 and about 90% v/v, about 0.01 and about 80% v/v, about 0.01 and about 70% v/v, about 0.01 and about 60% v/v, about 0.01 and about 50% v/v, about 0.01 and about 40% v/v, about 0.01 and about 30% v/v, about 0.01 and about 20% v/v, about 0.01 and about 10% v/v, about 0.01 and about 5% v/v, about 0.01 and about 1% v/v, about 0.01 and about 0.1% v/v, about 0.1 and about 95% v/v, about 0.1 and about 90% v/v, about 0.1 and about 80% v/v, about 0.1 and about 70% v/v, about 0.1 and about 60% v/v, about 0.1 and about 50% v/v, about 0.1 and about 40% v/v, about 0.1 and about 30% v/v, about 0.1 and about 20% v/v, about 0.1 and about 10% v/v, about 0.1 and about 5% v/v, about 0.1 and about 1% v/v, about 1 and about 95% v/v, about 1 and about 90% v/v, about 1 and about 80% v/v, about 1 and about 70% v/v, about 1 and about 60% v/v, about 1 and about 50% v/v, about 1 and about 40% v/v, about 1 and about 30% v/v, about 1 and about 20% v/v, about 1 and about 10% v/v, about 1 and about 5% v/v, about 5 and about 95% v/v, about 5 and about 90% v/v, about 5 and about 80% v/v, about 5 and about 70% v/v, about 5 and about 60% v/v, about 5 and about 50% v/v, about 5 and about 40% v/v, about 5 and about 30% v/v, about 5 and about 20% v/v, about 5 and about 10% v/v, about 10 and about 95% v/v, about 10 and about 90% v/v, about 10 and about 80% v/v, about 10 and about 70% v/v, about 10 and about 60% v/v, about 10 and about 50% v/v, about 10 and about 40% v/v, about 10 and about 30% v/v, about 10 and about 20% v/v, about 20 and about 95% v/v, about 20 and about 90% v/v, about 20 and about 80% v/v, about 20 and about 70% v/v, about 20 and about 60% v/v, about 20 and about 50% v/v, about 20 and about 40% v/v, about 20 and about 30% v/v, about 30 and about 95% v/v, about 30 and about 90% v/v, about 30 and about 80% v/v, about 30 and about 70% v/v, about 30 and about 60% v/v, about 30 and about 50% v/v, about 30 and about 40% v/v, about 40 and about 95% v/v, about 40 and about 90% v/v, about 40 and about 80% v/v, about 40 and about 70% v/v, about 40 and about 60% v/v, about 40 and about 50% v/v, about 50 and about 95% v/v, about 50 and about 90% v/v, about 50 and about 80% v/v, about 50 and about 70% v/v, about 50 and about 60% v/v, about 60 and about 95% v/v, about 60 and about 90% v/v, about 60 and about 80% v/v, about 60 and about 70% v/v, about 70 and about 95% v/v, about 70 and about 90% v/v, about 70 and about 80% v/v, about 80 and about 95% v/v, about 80 and about 90% v/v, or about 90 and about 95% v/v.

In some embodiments, the composition contains an excipient in an amount between about 0.01 and about 95% w/w, about 0.01 and about 90% w/w, about 0.01 and about 80% w/w, about 0.01 and about 70% w/w, about 0.01 and about 60% w/w, about 0.01 and about 50% w/w, about 0.01 and about 40% w/w, about 0.01 and about 30% w/w, about 0.01 and about 20% w/w, about 0.01 and about 10% w/w, about 0.01 and about 5% w/w, about 0.01 and about 1% w/w, about 0.01 and about 0.1% w/w, about 0.1 and about 95% w/w, about 0.1 and about 90% w/w, about 0.1 and about 80% w/w, about 0.1 and about 70% w/w, about 0.1 and about 60% w/w, about 0.1 and about 50% w/w, about 0.1 and about 40% w/w, about 0.1 and about 30% w/w, about 0.1 and about 20% w/w, about 0.1 and about 10% w/w, about 0.1 and about 5% w/w, about 0.1 and about 1% w/w, about 1 and about 95% w/w, about 1 and about 90% w/w, about 1 and about 80% w/w, about 1 and about 70% w/w, about 1 and about 60% w/w, about 1 and about 50% w/w, about 1 and about 40% w/w, about 1 and about 30% w/w, about 1 and about 20% w/w, about 1 and about 10% w/w, about 1 and about 5% w/w, about 5 and about 95% w/w, about 5 and about 90% w/w, about 5 and about 80% w/w, about 5 and about 70% w/w, about 5 and about 60% w/w, about 5 and about 50% w/w, about 5 and about 40% w/w, about 5 and about 30% w/w, about 5 and about 20% w/w, about 5 and about 10% w/w, about 10 and about 95% w/w, about 10 and about 90% w/w, about 10 and about 80% w/w, about 10 and about 70% w/w, about 10 and about 60% w/w, about 10 and about 50% w/w, about 10 and about 40% w/w, about 10 and about 30% w/w, about 10 and about 20% w/w, about 20 and about 95% w/w, about 20 and about 90% w/w, about 20 and about 80% w/w, about 20 and about 70% w/w, about 20 and about 60% w/w, about 20 and about 50% w/w, about 20 and about 40% w/w, about 20 and about 30% w/w, about 30 and about 95% w/w, about 30 and about 90% w/w, about 30 and about 80% w/w, about 30 and about 70% w/w, about 30 and about 60% w/w, about 30 and about 50% w/w, about 30 and about 40% w/w, about 40 and about 95% w/w, about 40 and about 90% w/w, about 40 and about 80% w/w, about 40 and about 70% w/w, about 40 and about 60% w/w, about 40 and about 50% w/w, about 50 and about 95% w/w, about 50 and about 90% w/w, about 50 and about 80% w/w, about 50 and about 70% w/w, about 50 and about 60% w/w, about 60 and about 95% w/w, about 60 and about 90% w/w, about 60 and about 80% w/w, about 60 and about 70% w/w, about 70 and about 95% w/w, about 70 and about 90% w/w, about 70 and about 80% w/w, about 80 and about 95% w/w, about 80 and about 90% w/w, or about 90 and about 95% w/w.

Methods of Preparation

Also provided are methods of preparing the topical compositions herein. In some embodiments, the compositions of the present disclosure are prepared by any suitable method. In some embodiments, a composition of the present disclosure are prepared by combining the components of the composition. In some embodiments, all components are combined simultaneously. In some embodiments, each component is combined individually, for example in a specified order. The methods of combining provided herein may include, but are not limited to, mixing, admixing, vortexing, emulsifying, or compounding.

In some embodiments, the method of preparing a composition provided herein comprises combining a first antibacterial, a first antifungal, and a first anti-inflammatory. In some embodiments, the method of preparing a composition provided herein comprises combining a first antibacterial, a second antibacterial, a first antifungal, and a first anti-inflammatory. In some embodiments, the method of preparing a composition provided herein comprises combining a first antibacterial, a first antifungal, a second antifungal, and a first anti-inflammatory. In some embodiments, the method of preparing a composition provided herein comprises combining a first antibacterial, a first antifungal, a first anti-inflammatory, and a second anti-inflammatory. In some embodiments, the method of preparing a composition provided herein comprises combining a first antibacterial, a second antibacterial, a first antifungal, a second antifungal, and a first anti-inflammatory. In some embodiments, the method of preparing a composition provided herein comprises combining a first antibacterial, a second antibacterial, a first antifungal, a second antifungal, and a first anti-inflammatory. In some embodiments, the method of preparing a composition provided herein comprises combining a first antibacterial, a first antifungal, a second antifungal, a first anti-inflammatory, and a second anti-inflammatory. In some embodiments, the method of preparing a composition provided herein comprises combining a first antibacterial, a second antibacterial, a first antifungal, a second antifungal, a first anti-inflammatory, and a second anti-inflammatory.

In some embodiments, one or more of the components to be combined are already be formulated for topical use. For example, the anti-inflammatory to be combined may be an anti-inflammatory formulation such as a 1% hydrocortisone acetate cream.

In some embodiments, the method of preparing a composition provided herein comprises combining a terbinafine 1% cream, a clotrimazole 1% cream, a mupirocin 2% cream, and a hydrocortisone 1% cream. In some embodiments, the method of preparing a composition provided herein comprises combining a terbinafine 1% cream, a clotrimazole 1% cream, a mupirocin 2% cream, and a hydrocortisone 1% cream in equal parts v/v. In some embodiments, the method of preparing a composition provided herein comprises combining a terbinafine 1% cream, a clotrimazole 1% cream, a mupirocin 2% cream, and a hydrocortisone 1% cream in equal parts w/w. In some embodiments, the method of preparing a composition provided herein comprises combining a clotrimazole 1% cream, a hydrocortisone acetate 1% cream, a mupirocin calcium 2% cream, and a terbinafine hydrochloride 1% cream in equal parts v/v.

Administration and Use

In some embodiments, the subject is a human. In some embodiments, the subject is a human having an infection or inflammation associated with an infection. In some embodiments, the subject is a human having a fungal infection, a yeast infection, a bacterial infection, inflammation, or any combination thereof. In some embodiments, the fungal infection, the yeast infection, the bacterial infection, the inflammation, or the combination thereof affects the subject's skin, nails, or both thereof. In some embodiments, the fungal infection is a skin infection, a nail infection or both a nail and skin infection. In some embodiments, the yeast infection comprises a skin infection, a nail infection, or both a nail and skin infection. In some embodiments, the bacterial infection comprises a skin infection, a nail infection, or both a nail and skin infection. In some embodiments, the inflammation comprises skin inflammation, nail inflammation, or both nail and skin inflammation.

Provided herein are methods of treating or preventing an infection or inflammation associated with an infection. In some embodiments, the condition to be treated or prevented is a fungal infection, a yeast infection, a bacterial infection, inflammation, or any combination thereof, the method comprising topically administering to a subject any composition provided herein. In some embodiments, the condition to be treated or prevented is athlete's foot, jock itch, or ringworm. In some embodiments, the condition to be treated or prevented is treats or prevents athlete's foot. In some embodiments, the condition to be treated or prevented is treats athlete's foot. In some embodiments, the condition to be treated or prevented affects the subject's skin. In some embodiments, the condition to be treated or prevented affects one or more of the subject's nails. In some embodiments, the condition to be treated or prevented affects the subject's skin and one or more of the subject's nails. In some embodiments, the composition is topically administered to the subject's skin. In some embodiments composition is topically administered to one or more of the subject's nails. In some embodiments, the composition is topically administered to the subject's skin and one or more of the subject's nails. In some embodiments, the topical administration occurs at, or as close as possible, to the site of the infection and/or inflammation. In some embodiments, the present disclosure provides methods of treating a subject's skin, nails, or both skin and nails.

In some embodiments, the composition is administered at least one, two, three, four, or five times per day. In some embodiments, the composition is administered one, two or three times per day. In some embodiments, the composition is administered twice a day.

In some embodiments, the composition is administered at least 1, 2, 3, 4, 5, 6, 7, 8, 9, 10, 11, 12, 13, 14, 15, 16, 17, 18, 19, 20, 21, 25, 28, 30, or 35 times per week. In some embodiments, the composition is administered between about 1 and about 35 times per week, about 1 and about 28 times per week, about 1 and about 21 times per week, about 1 and about 14 times per week, about 1 and about 7 times per week, about 7 and about 35 times per week, about 7 and about 28 times per week, about 7 and about 21 times per week, about 7 and about 14 times per week, about 14 and about 35 times per week, about 14 and about 28 times per week, about 14 and about 21 times per week, about 21 and about 35 times per week, about 21 and about 28 times per week, or about 28 and 35 times per week. In some embodiments, the composition is administered about 1 time per week, about 7 times per week, about 14 times per week, about 21 times per week, about 28 times per week, or about 35 times per week.

In some embodiments, a single administration comprises administering about one mL, about two mL, about three mL, about four mL, about five mL, about six mL, about seven mL, about eight mL, about nine mL or about ten mL of the solid pharmaceutical composition. In some embodiments, a single administration comprises administering about one gram, about two grams, about three grams, about four grams, about five grams, about six grams, about seven grams, about eight grams, about nine grams, or about ten grams of the solid pharmaceutical composition.

In some embodiments, the administration is performed for a duration of about 1 day to about 3 months, about 1 day to about 10 weeks, about 1 day to about 8 weeks, about 1 day to about 6 weeks, about 1 day to about 5 weeks, about 1 day to about 4 weeks, about 1 day to about 3 weeks, about 1 day to about 2 weeks, about 1 day to about 10 days, about 1 day to about 8 days, about 1 day to about 1 week, about 1 day to about 6 days, about 1 day to about 5 days, about 1 day to about 4 days, about 1 day to about 3 days, about 1 day to about 2 days, 2 days to about 3 months, about 2 days to about 10 weeks, about 2 days to about 8 weeks, about 2 days to about 6 weeks, about 2 days to about 5 weeks, about 2 days to about 4 weeks, about 2 days to about 3 weeks, about 2 days to about 2 weeks, about 2 days to about 10 days, about 2 days to about 8 days, about 2 days to about 1 week, about 2 days to about 6 days, about 2 days to about 5 days, about 2 days to about 4 days, about 2 days to about 3 days, about 3 days to about 3 months, about 3 days to about 10 weeks, about 3 days to about 8 weeks, about 3 days to about 6 weeks, about 3 days to about 5 weeks, about 3 days to about 4 weeks, about 3 days to about 3 weeks, about 3 days to about 2 weeks, about 3 days to about 10 days, about 3 days to about 8 days, about 3 days to about 1 week, about 3 days to about 6 days, about 3 days to about 5 days, about 3 days to about 4 days, about 4 days to about 3 months, about 4 days to about 10 weeks, about 4 days to about 8 weeks, about 4 days to about 6 weeks, about 4 days to about 5 weeks, about 4 days to about 4 weeks, about 4 days to about 3 weeks, about 4 days to about 2 weeks, about 4 days to about 10 days, about 4 days to about 8 days, about 4 days to about 1 week, about 4 days to about 6 days, about 4 days to about 5 days, about 5 days to about 3 months, about 5 days to about 10 weeks, about 5 days to about 8 weeks, about 5 days to about 6 weeks, about 5 days to about 5 weeks, about 5 days to about 4 weeks, about 5 days to about 3 weeks, about 5 days to about 2 weeks, about 5 days to about 10 days, about 5 days to about 8 days, about 5 days to about 1 week, about 5 days to about 6 days, about 6 days to about 3 months, about 6 days to about 10 weeks, about 6 days to about 8 weeks, about 6 days to about 6 weeks, about 6 days to about 5 weeks, about 6 days to about 4 weeks, about 6 days to about 3 weeks, about 6 days to about 2 weeks, about 6 days to about 10 days, about 6 days to about 8 days, about 6 days to about 1 week, about 1 week to about 3 months, about 1 week to about 10 weeks, about 1 week to about 8 weeks, about 1 week to about 6 weeks, about 1 week to about 5 weeks, about 1 week to about 4 weeks, about 1 week to about 3 weeks, about 1 week to about 2 weeks, about 1 week to about 10 days, about 1 week to about 8 days, about 8 days to about 3 months, about 8 days to about 10 weeks, about 8 days to about 8 weeks, about 8 days to about 6 weeks, about 8 days to about 5 weeks, about 8 days to about 4 weeks, about 8 days to about 3 weeks, about 8 days to about 2 weeks, about 8 days to about 10 days, about 10 days to about 3 months, about 10 days to about 10 weeks, about 10 days to about 8 weeks, about 10 days to about 6 weeks, about 10 days to about 5 weeks, about 10 days to about 4 weeks, about 10 days to about 3 weeks, about 10 days to about 2 weeks, about 2 weeks to about 3 months, about 2 weeks to about 10 weeks, about 2 weeks to about 8 weeks, about 2 weeks to about 6 weeks, about 2 weeks to about 5 weeks, about 2 weeks to about 4 weeks, about 2 weeks to about 3 weeks, about 3 weeks to about 3 months, about 3 weeks to about 10 weeks, about 3 weeks to about 8 weeks, about 3 weeks to about 6 weeks, about 3 weeks to about 5 weeks, about 3 weeks to about 4 weeks, about 4 weeks to about 3 months, about 4 weeks to about 10 weeks, about 4 weeks to about 8 weeks, about 4 weeks to about 6 weeks, about 4 weeks to about 5 weeks, 5 weeks to about 3 months, about 5 weeks to about 10 weeks, about 5 weeks to about 8 weeks, about 5 weeks to about 6 weeks, about 6 weeks to about 3 months, about 6 weeks to about 10 weeks, about 6 weeks to about 8 weeks, about 8 weeks to about 3 months, about 8 weeks to about 10 weeks, or about 10 weeks to about 3 months, In some embodiments the administration is performed for a duration of 3 months or less, about 10 weeks or less, about 8 weeks or less, about 7 weeks or less, about 6 weeks or less, about 5 weeks or less, about 4 weeks or less, about 3 weeks or less, about 2 weeks or less, about 10 days or less, about 9 days or less, about 8 days or less, about 7 days or less, about 6 days or less, about 5 days or less, about 4 days or less, about 3 days or less, about 2 days or less, or about 1 day or less.

In some embodiments, the administration is performed for a duration of about 1 day, about 2 days, about 3 days, about 4 days, about 5 days, about 6 days, about 7 days, about 8 days about 9 days, about 10 days, about 2 weeks, about 3 weeks, about 4 weeks, about 5 weeks, about 6 weeks, about 7 weeks, about 8 weeks, about 10 weeks, or about 3 months.

In some embodiments, the amount of the composition administered, and the frequency and duration of administration may vary according to factors such as the identity and severity of the condition, the age, sex, and weight of the subject, and the ability of the composition to efficaciously treat or prevent the subject. In some embodiments, for any particular subject, the method of administration can be adjusted over time according to the individual need and the professional judgment of the person administering or supervising the administration of the compositions.

ENUMERATED EMBODIMENTS

The following non-limiting enumerated embodiments are only exemplary embodiments of the invention provided herein and do not limit any aspects of the present disclosure in any way.

Embodiment I-1: A composition formulated for topical use comprising a first antibacterial, a first antifungal, and a first anti-inflammatory Embodiment I-2: The composition of Embodiment I-1, wherein the first antibacterial is a topical antibacterial.

Embodiment I-3: The composition of Embodiment I-1 or Embodiment I-2, wherein the first antibacterial is mupirocin, neomycin, bacitracin, polymyxin B, sulfadiazine, clindamycin, gentamicin, erythromycin, or metronidazole, or a pharmaceutically acceptable salt thereof.

Embodiment I-4: The composition of Embodiment I-3, wherein the first antibacterial is mupirocin or a pharmaceutically acceptable salt thereof.

Embodiment I-5: The composition of any one of Embodiments I-1-4, wherein the composition contains the first antibacterial in an amount of from about 0.05% v/v to about 2% v/v.

Embodiment I-6: The composition of Embodiment I-5, wherein the composition contains the first antibacterial in an amount of about 0.5% v/v.

Embodiment I-7: The composition of any one of Embodiments I-1-6, comprising a second antibacterial.

Embodiment I-8: The composition of Embodiment I-7, wherein the composition contains the second antibacterial in an amount of from about 0.1% v/v to about 1% v/v.

Embodiment I-9: The composition of Embodiment I-7 or Embodiment I-8, wherein the composition contains the second antibacterial in an amount of about 0.5% v/v.

Embodiment I-10: The composition of any one of Embodiments I-7-9, wherein the second antibacterial is mupirocin, bacitracin, polymyxin B, sulfadiazine, clindamycin, gentamicin, erythromycin, or metronidazole, or a pharmaceutically acceptable salt thereof.

Embodiment I-11: The composition of any one of Embodiments I-1-10, wherein the first antifungal is a topical antifungal.

Embodiment I-12: The composition of Embodiment I-11, wherein the first antifungal is butenafine, ciclopirox, clotrimazole, econazole, ketoconazole, miconazole, naftifine, nystatin, oxiconazole, sertaconazole, terbinafine, or tolnaftate, or a pharmaceutically acceptable salt thereof.

Embodiment I-13: The composition of Embodiment I-12, wherein the first antifungal is terbinafine or clotrimazole, or a pharmaceutically acceptable salt thereof.

Embodiment I-14: The composition of any one of Embodiment I-1-13, wherein the composition contains the first antifungal in an amount of from about 0.05% v/v to about 1.0% v/v.

Embodiment I-15: The composition of Embodiment I-14, wherein the composition contains the first antifungal in an amount of about 0.25% v/v.

Embodiment I-16: The composition of any one of Embodiments I-1-15, comprising a second antifungal.

Embodiment I-17: The composition of Embodiment I-16, wherein the second antifungal is butenafine, ciclopirox, clotrimazole, econazole, ketoconazole, miconazole, naftifine, nystatin, oxiconazole, sertaconazole, terbinafine, or tolnaftate, or a pharmaceutically acceptable salt thereof.

Embodiment I-18: The composition of Embodiment I-17, wherein the first antifungal is terbinafine, or a pharmaceutically acceptable salt thereof, and the second antifungal is clotrimazole, or a pharmaceutically acceptable salt thereof.

Embodiment I-19: The composition of any one of Embodiments I-16-18, wherein the composition contains the second antifungal in an amount of from about 0.05% v/v to about 1.0% v/v.

Embodiment I-20: The composition of Embodiment I-19, wherein the composition contains the second antifungal in an amount of about 0.25% v/v.

Embodiment I-21: The composition of any one of Embodiments I-1-20, wherein the anti-inflammatory is a topical anti-inflammatory.

Embodiment I-22: The composition of any one of Embodiments I-1-21, wherein the first anti-inflammatory is a corticosteroid.

Embodiment I-23: The composition of any one of Embodiments I-1-22, wherein the first anti-inflammatory is hydrocortisone, alclometasone, clocortolone, desonide, bethamethasone, fluocinolone, or triamcinolone, or a pharmaceutically acceptable salt thereof.

Embodiment I-24: The composition of Embodiment I-23, wherein the first anti-inflammatory is hydrocortisone or a pharmaceutically acceptable salt thereof.

Embodiment I-25: The composition of Embodiment I-24, wherein the first anti-inflammatory is hydrocortisone acetate.

Embodiment I-26: The composition of any one of Embodiments I-1-25, wherein the composition contains the first anti-inflammatory in an amount of from about 0.05% v/v to about 1.0% v/v.

Embodiment I-27: The composition of Embodiment I-26, wherein the composition contains the first anti-inflammatory in an amount of about 0.25% v/v.

Embodiment I-28: The composition of any one of Embodiments I-1-27, comprising a second anti-inflammatory.

Embodiment I-29: The composition of Embodiment I-28, wherein the composition contains the second anti-inflammatory in an amount of from about 0.05% v/v to about 1.0% v/v.

Embodiment I-30: The composition of Embodiment I-29, wherein the composition contains the second anti-inflammatory in an amount of about 0.5% v/v.

Embodiment I-31: The composition of any one of Embodiments I-28-30, wherein the second anti-inflammatory is hydrocortisone, alclometasone, clocortolone, desonide, bethamethasone, fluocinolone, or triamcinolone, or a pharmaceutically acceptable salt thereof.

Embodiment I-32: The composition of Embodiment I-1, wherein the composition comprises mupirocin, terbinafine, clotrimazole, and hydrocortisone acetate.

Embodiment I-33: The composition of Embodiment I-32, wherein the composition consists essentially of mupirocin, terbinafine, clotrimazole, and hydrocortisone acetate.

Embodiment I-34: The composition of Embodiment I-32 or Embodiment I-33, wherein the composition contains the mupirocin in an amount of about 0.5% v/v.

Embodiment I-35: The composition of any one of Embodiments I-32-34, wherein the composition contains the terbinafine in an amount of about 0.25% v/v.

Embodiment I-36: The composition of any one of Embodiments I-32-35, wherein the composition contains the clotrimazole in an amount of about 0.25% v/v.

Embodiment I-37: The composition of any one of Embodiments I-32-36, wherein the composition contains the hydrocortisone in an amount of about 0.25% v/v.

Embodiment I-38: A composition formulated for topical use, comprising mupirocin, or a pharmaceutically acceptable salt thereof, in an amount of between about 0.2 and about 0.75% v/v, terbinafine, or a pharmaceutically acceptable salt thereof, in an amount between about 0.1 and about 0.5% v/v, clotrimazole, or a pharmaceutically acceptable salt thereof, in an amount between about 0.1 and about 0.5% v/v, and hydrocortisone, or a pharmaceutically acceptable salt thereof, in an amount between about 0.1 and about 0.5% v/v.

Embodiment I-39: The composition of Embodiment I-38, wherein the composition consists essentially of about 0.5% v/v of the mupirocin, or the pharmaceutically acceptable salt thereof, about 0.25% v/v of the terbinafine, or the pharmaceutically acceptable salt thereof, about 0.25% v/v of the clotrimazole, or the pharmaceutically acceptable salt thereof, and about 0.25% v/v of the hydrocortisone, or the pharmaceutically acceptable salt thereof.

Embodiment I-40: A composition formulated for topical use, comprising mupirocin calcium in an amount of about 0.5% v/v, terbinafine hydrochloride in an amount of about 0.25% v/v, clotrimazole in an amount of about 0.25% v/v, and hydrocortisone acetate in an amount of about 0.25% v/v.

Embodiment I-41: The composition of Embodiment I-40, wherein the composition consists essentially of the mupirocin calcium, terbinafine hydrochloride, clotrimazole, and hydrocortisone acetate.

Embodiment I-42: The composition of any one of Embodiments I-1-41, wherein the composition is in the form of a cream, an ointment, a lotion, or a gel.

Embodiment I-43: The composition of Embodiment I-42, wherein the composition is in the form of a cream.

Embodiment I-44: The composition of any one of Embodiments I-1-43 for use as a medicament.

Embodiment I-45: The composition of any one of Embodiments I-1-43 for use in treating a fungal infection, a yeast infection, a bacterial infection, inflammation, or any combination thereof.

Embodiment I-46: The composition of Embodiment I-44 or 45 for use in treating athlete's foot, jock itch, or ringworm.

Embodiment I-47: The composition of any one of Embodiments I-44-46 for use in treating athlete's foot.

Embodiment I-48: A method of preparing the composition of any one of Embodiments I-1-47, the method comprising combining the first antibacterial, the first antifungal, and the first anti-inflammatory.

Embodiment I-49: A method of treating or preventing a fungal infection, a yeast infection, a bacterial infection, inflammation, or any combination thereof, the method comprising topically administering to a subject the composition of any one of Embodiments I-1-43.

Embodiment I-50: The method of Embodiment I-49, wherein the method treats or prevents athlete's foot, jock itch, or ringworm.

Embodiment I-51: The method of Embodiment I-49 or 50, wherein the method treats or prevents athlete's foot.

Embodiment I-52: The method of any one of Embodiments I-49 to 51, wherein the method treats athlete's foot.

Embodiment I-53: The method of any one of Embodiments I-49-52, wherein the method comprises administering the composition once daily, twice daily, or three times daily.

Embodiment I-54: The method of any one of Embodiments I-49-53, wherein the administration is performed for a duration of from about 1 day to about 4 weeks.

Embodiment I-55: The method of any one of Embodiments I-49-54, wherein the administration is performed for a duration of about 1 week, about 10 days, about 2 weeks, about 3 weeks, or about 4 weeks.

Embodiment I-56: Use of the composition of any one of Embodiments I-1-43 for the treatment of athlete's foot, jock itch, or ringworm.

Embodiment I-57: The use of Embodiment I-56, wherein the composition is used for the treatment of athlete's foot.

Embodiment I-58: Use of a first antibacterial, a first antifungal, and a first anti-inflammatory for the manufacture of a medicament for the treatment or prevention of a fungal infection, a yeast infection, a bacterial infection, inflammation, or any combination thereof.

Embodiment I-59: The use of Embodiment I-58, wherein the medicament is for the treatment or prevention of athlete's foot, jock itch, or ringworm.

Embodiment I-60: The use of Embodiment I-58 or 59, wherein the medicament is for the treatment or prevention of athlete's foot.

Embodiment I-61: The use of any one of Embodiments I-58-60, wherein the medicament is for the treatment of athlete's foot.

Embodiment I-62: The use of any one of Embodiments I-58-61, wherein the medicament comprises the composition of any one of Embodiments I-1-43.

EXAMPLES

The following Examples are merely illustrative and do not limit any aspects of the present disclosure in any way.

Exemplary Composition 1 was prepared by combining equal parts v/v clotrimazole 1%, hydrocortisone acetate 1%, mupirocin calcium 2%, and terbinafine hydrochloride 1% creams to yield a white cream.

Example 1: A 49-year-old female developed an itchy red skin rash on one shoulder and started treated with Exemplary Composition 1 three days later. Subject topically applied the composition to the affected area twice a day for four days. The skin rash resolved after four days of treatment and did not return for at least 30 days.

Figure 1B:

Example 2: A 17-year-old female developed an itchy red skin rash on her neck and started treatment with Exemplary Composition 1 thirteen days later. Subject topically applied the composition to the affected area twice a day for seven days. The skin rash resolved after seven days of treatment and did not return for at least 18 days. FIGS. 1A and 1B show the subject before and after treatment, respectively.

Example 3: A 62-year-old male suffered with jock itch for 3 to 4 months. The condition did not respond to 1% Tolnaftate—an over-the-counter topical antifungal. Subject topically applied Exemplary Composition 1 to the affected area twice a day for three days. The condition resolved after three days of treatment and did not return for at least 3 months.

Example 4: A 61-year-old male suffered with athlete's feet for several months. The condition did not respond to over-the-counter topical antifungals. Subject topically applied Exemplary Composition 1 to the affected area twice a day for one day. The condition resolved after one day of treatment and did not return for at least 2 months.

Figure 2A:
FIGS. 2A and 2B show the subject of Example 5's affected toenails both before (FIG. 2A; photo dated Feb. 19, 2024) and after (FIG. 2B; photo dated Mar. 3, 2024) treatment with Exemplary Composition 1.
Figure 2B:

Example 5: A 7-year-old male suffered with athlete's feet for several months. Subject applied Exemplary Composition 1 to the affected area twice a day for ten days. The condition resolved after ten days of treatment and did not return for at least for at least 2 months. FIGS. 2A and 2B show the subject before and after treatment, respectively.

Example 6: A 59-year-old male suffered with athlete's feet for several months. The condition did not respond to topical treatment using econazole nitrate cream 1% and oxiconazole 1% lotion. Subject topically applied Exemplary Composition 1 to the affected area twice a day for two days. The condition resolved after two days of treatment and did not return for at least 3 months.

Figure 3A:
FIGS. 3A and 3B show the subject of Example 8's affected toenails both before (FIG. 3A; photo dated Feb. 6, 2024) and after (FIG. 3B; photo dated May 15, 2024) treatment with Exemplary Composition 1.
Figure 3B:

Example 8: A 69-year-old female suffered with fungal toenails for 3 years, with the condition deteriorating over time. Prior treatments of soaking in apple cider vinegar and weekly oral administration of fluconazole did not improve the condition. Subject topically applied Exemplary Composition 1 to the affected area twice a day for 3 months. The condition notably improved after 3 months of treatment. FIGS. 3A and 3B show the subject before and after treatment, respectively.

The above Examples demonstrate that the composition of Exemplary Composition 1 efficaciously treats a variety of conditions.

What is claimed is:

1. A composition formulated for topical use comprising active ingredients and one or more excipients, wherein the active ingredients consist of mupirocin, or a pharmaceutically acceptable salt thereof, in an amount of between about 0.2 and about 0.75% v/v, terbinafine, or a pharmaceutically acceptable salt thereof, in an amount between about 0.1 and about 0.5% v/v, clotrimazole, or a pharmaceutically acceptable salt thereof, in an amount between about 0.1 and about 0.5% v/v, and hydrocortisone, or a pharmaceutically acceptable salt thereof, in an amount between about 0.1 and about 0.5% v/v.

2. The composition of claim 1, wherein the active ingredients consist of about 0.5% v/v of the mupirocin, or the pharmaceutically acceptable salt thereof, about 0.25% v/v of the terbinafine, or the pharmaceutically acceptable salt thereof, about 0.25% v/v of the clotrimazole, or the pharmaceutically acceptable salt thereof, and about 0.25% v/v of the hydrocortisone, or the pharmaceutically acceptable salt thereof.

3. The composition of claim 1, wherein the composition is in the form of a cream, an ointment, a lotion, or a gel.

4. The composition of claim 1, wherein the mupirocin, or the pharmaceutically acceptable salt thereof, in an amount of about 0.5% v/v.

5. The composition of claim 1, wherein the clotrimazole, or the pharmaceutically acceptable salt thereof, in an amount of about 0.25% v/v.

6. The composition of claim 1, wherein the terbinafine, or the pharmaceutically acceptable salt thereof, in an amount of about 0.25% v/v.

7. The composition of claim 1, wherein the hydrocortisone, or the pharmaceutically acceptable salt thereof, in an amount of about 0.25% v/v.

8. The composition of claim 1, wherein the one or more excipients is selected from purified water, ethyl alcohol, benzyl alcohol, cetyl alcohol, stearyl alcohol, cetostearyl alcohol, cetyl alcohol, octyldodecanol, cetyl palmitate, isopropyl myristate, polysorbate 60, sodium hydroxide, sodium monostearate, glyceryl monostearate, corn oil, chamomile flower oil, mineral oil, paraffin, petrolatum, maltodextrin, phenoxyethanol, polyoxyl 20 cetostearyl ether, xanthan gum, methylparaben, propylene glycol, propylparaben, sodium lauryl sulfate, sodium cetostearyl sulfate, aloe vera gel, glycerin, citric acid, vitamin A palmitate, cholecalciferol, or alpha-tocopherol acetate.

9. The composition of claim 1, wherein the active ingredients consist of mupirocin calcium in an amount of about 0.5% v/v, terbinafine hydrochloride in an amount of about 0.25% v/v, clotrimazole in an amount of about 0.25% v/v, and hydrocortisone acetate in an amount of about 0.25% v/v.

10. A method of treating a rash, jock itch, Athlete's foot, or fungal toenails, the method comprising topically administering to a subject the composition of claim 1.

11. The method of claim 10, wherein the method treats athlete's foot, or jock itch.

12. The method of claim 11, wherein the method treats athlete's foot.

13. The method of claim 10, wherein the method comprises administering the composition once daily, twice daily, or three times daily.

14. The method of claim 10, wherein the administration is performed for a duration of from about 1 day to about 4 weeks.

* * * * *